(12) United States Patent
Cherian et al.

(10) Patent No.: US 8,860,152 B2
(45) Date of Patent: Oct. 14, 2014

(54) INTEGRATED CHEMICAL SENSOR

(75) Inventors: Suman Cherian, Singapore (SG); Olivier Le Neel, Singapore (SG)

(73) Assignee: STMicroelectronics Pte Ltd., Singapore (SG)

( * ) Notice: Subject to any disclaimer, the term of this patent is extended or adjusted under 35 U.S.C. 154(b) by 8 days.

(21) Appl. No.: 13/285,911

(22) Filed: Oct. 31, 2011

(65) Prior Publication Data

US 2012/0168882 A1 Jul. 5, 2012

Related U.S. Application Data

(60) Provisional application No. 61/428,826, filed on Dec. 30, 2010.

(51) Int. Cl.
*H01L 31/058* (2006.01)
*G01N 33/487* (2006.01)

(52) U.S. Cl.
CPC ............... *G01N 33/48785* (2013.01)
USPC .................. 257/414; 257/E27.122; 257/467

(58) Field of Classification Search
USPC .................. 257/414, 467, E27.122
See application file for complete search history.

(56) References Cited

U.S. PATENT DOCUMENTS

| | | | |
|---|---|---|---|
| 5,018,395 A | 5/1991 | Hickox et al. | |
| 5,204,541 A * | 4/1993 | Smayling et al. | ............. 257/138 |
| 5,640,013 A * | 6/1997 | Ishikawa et al. | ............ 250/338.4 |
| 6,085,576 A | 7/2000 | Sunshine et al. | |
| 6,448,695 B2 | 9/2002 | Milsom | |
| 6,467,332 B1 | 10/2002 | Bertschi et al. | |
| 6,649,357 B2 | 11/2003 | Bryan et al. | |
| 6,821,729 B2 | 11/2004 | Ackley et al. | |
| 6,883,364 B2 | 4/2005 | Sunshine et al. | |
| 6,933,807 B2 | 8/2005 | Marksteiner et al. | |
| 7,071,073 B2 | 7/2006 | Villa et al. | |
| 7,189,314 B1 | 3/2007 | Pace et al. | |
| 7,294,536 B2 | 11/2007 | Villa et al. | |
| 7,364,896 B2 | 4/2008 | Schembri | |
| 7,368,312 B1 * | 5/2008 | Kranz et al. | ..................... 438/48 |
| 7,651,868 B2 | 1/2010 | McDevitt et al. | |
| 2003/0062807 A1 | 4/2003 | Takeuchi et al. | |
| 2003/0201450 A1* | 10/2003 | Yamazaki et al. | .............. 257/88 |
| 2004/0172798 A1 | 9/2004 | Ruby et al. | |
| 2005/0208696 A1 | 9/2005 | Villa et al. | |

(Continued)

FOREIGN PATENT DOCUMENTS

| | | |
|---|---|---|
| EP | 0 822 579 A1 | 2/1998 |
| EP | 1 324 382 A1 | 7/2003 |
| EP | 1 403 383 A1 | 3/2004 |

OTHER PUBLICATIONS

Cherian et al., "Chemical Sensor With Replaceable Sample Collection Chip," U.S. Appl. No. 13/285,867, filed Oct. 31, 2011, 39 pages.

(Continued)

*Primary Examiner* — Amar Movva
(74) *Attorney, Agent, or Firm* — Seed IP Law Group PLLC

(57) ABSTRACT

A integrated circuit die includes a chemical sensor, a thermal sensor, and a humidity sensor formed therein. The chemical sensor, thermal sensor, and humidity sensor include electrodes formed in a passivation layer of the integrated circuit die. The integrated circuit die further includes transistors formed in a monocrystaline semiconductor layer.

22 Claims, 22 Drawing Sheets

(56) References Cited

U.S. PATENT DOCUMENTS

| | | | |
|---|---|---|---|
| 2006/0125489 A1 | 6/2006 | Feucht et al. | |
| 2006/0197118 A1* | 9/2006 | Migliorato et al. | 257/253 |
| 2006/0257286 A1 | 11/2006 | Adams | |
| 2007/0290235 A1* | 12/2007 | Lehmann et al. | 257/253 |
| 2010/0107739 A1 | 5/2010 | Marra | |
| 2010/0163410 A1 | 7/2010 | Mastromatteo et al. | |
| 2010/0170324 A1 | 7/2010 | Mastrmatteo et al. | |
| 2011/0209524 A1 | 9/2011 | Ziglioli et al. | |
| 2011/0318840 A1 | 12/2011 | Ziglioli et al. | |
| 2012/0171713 A1 | 7/2012 | Cherian et al. | |

OTHER PUBLICATIONS

Cherian et al., "Single Chip Having the Chemical Sensor and Electronics on the Same Die," U.S. Appl. No. 13/285,894, filed Oct. 31, 2011, 35 pages.

Hwang et al., "CMOS VLSI Potentiostat for Portable Environmental Sensing Applications," *IEEE Sensors Journal* 10(4):820-821, Apr. 2010.

Schienle et al., "A Fully Electronic DNA Sensor With 128 Positions and In-Pixel A/D Conversion," *IEEE Journal of Solid-State Circuits* 39(12):2438-2445, Dec. 2004.

Turner et al., "A CMOS Potentiostat for Amperometric Chemical Sensors," *IEEE Journal of Solid-State Circuits*, SC-22(3):473-478, Jun. 1987.

Yang et al., "Amperometric Electrochemical Microsystem for a Miniaturized Protein Biosensor Array," *IEEE Transactions on Biomedical Circuits and Systems* 3(3):160-168, Jun. 2009.

Zhang et al., "Electrochemical Array Microsystem with Integrated Potentiostat," *IEEE Sensors*, pp. 385-388, 2005.

Benetti et al., "Chemical Sensor Based on Thin Film Bulk Acoustic Wave Resonator (TFBAR)," Proceedings of the 10th Italian Conference on Sensors and Microsystems, Firenze, Italy, pp. 326-331, Feb. 15-17, 2005.

D'amico et al., "Olfactometric Apparatus Based on Oscillating Crystal Sensors Functionalised With Tetrapyrrolic Macrocycles and Provided With Electronics for Conditioning and Reading the Signals, Communicating With a PC, Managing Through a Software and Analysis and Displaying the Data," Italian Patent Application No. RM2001A000455, filed Jul. 26, 2001, 20 pages w/ English translation.

Matsumoto et al., "Influence of Underlayer Materials on Preferred Orientations of Sputter-Deposited AlN/Mo Bilayers for Film Bulk Acoustic Wave Resonators," *Japanese Journal of Applied Physics* 43(12):8219-8222, 2004.

Richter et al., "A High Performance Silicon Micropump for Fuel Handling in DMFC Systems," proceedings of the Fuel Cell Seminar, Miami Beach, FL, USA, pp. 272-275, Nov. 3-7, 2003.

Rosenbaum, "Bulk Acoustic Wave Theory and Devices," Boston, MA: Artech House, 1988, 7 pages.

Kraver et al., "A mixed-signal sensor interface microinstrument," *Sensors and Actuators A 91*:266-277, 2001.

* cited by examiner

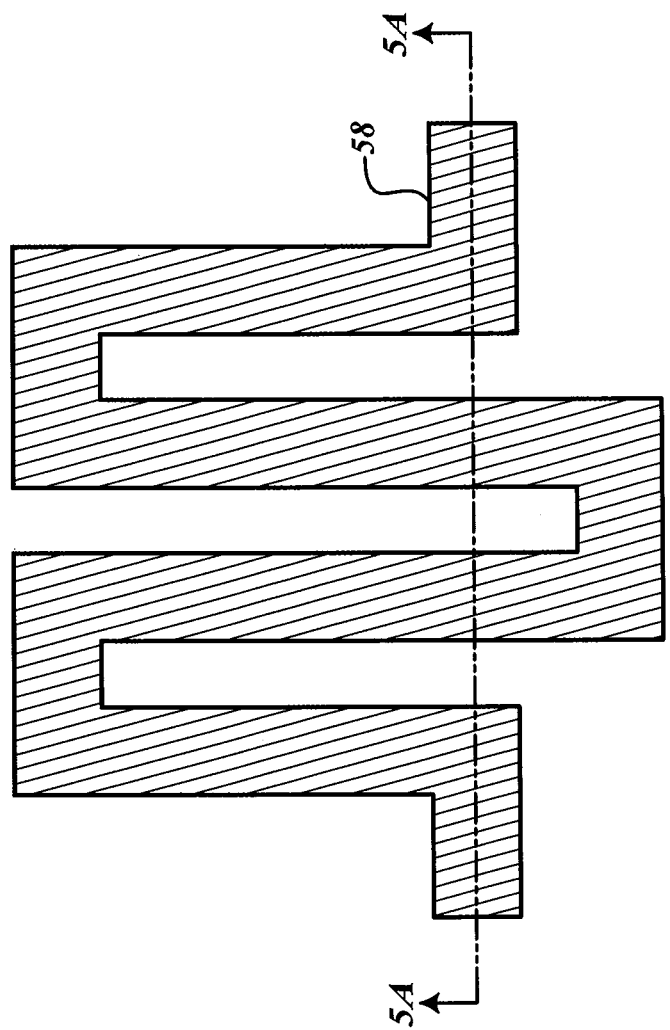

INTEGRATED CHEMICAL SENSOR

CROSS-REFERENCE TO RELATED APPLICATION

This application claims the benefit under 35 U.S.C. §119 (e) of U.S. Provisional Patent Application No. 61/428,826 filed Dec. 30, 2010 and is incorporated herein by reference in its entirety.

BACKGROUND

1. Technical Field

The present disclosure relates to a chemical sensor formed in a integrated circuit die.

2. Description of the Related Art

Chemical sensors are used in a variety of applications. Chemical sensors are used in medical applications, industrial applications, automotive applications, security applications, and domestic applications. Some examples of chemical sensors are blood glucose sensors, carbon dioxide detectors, automobile exhaust emission monitors, radon detectors, carbon monoxide detectors, explosives detectors, and a large variety of other applications.

In the past, many chemical sensors have been large and relatively expensive. Some chemical sensors are used in applications in which they may only be used a single time. Such single use sensors are typically used in biomedical applications. It can be very expensive to replace relatively large chemical detection system after each use.

BRIEF SUMMARY

One embodiment is a integrated circuit die including a chemical sensor. The integrated circuit die includes a monocrystaline semiconductor substrate, a dielectric layer formed on the monocrystaline semiconductor substrate, and metal interconnections formed in the dielectric layer. A first passivation layer is formed on the dielectric layer and the metal interconnections.

In one embodiment a chemical sensor is formed on the first passivation layer. A second passivation layer is formed on the first passivation layer and the chemical sensor. An opening is formed in the passivation layer to expose a portion of the chemical sensor to the surrounding environment. The chemical sensor is configured to react with a selected chemical. The chemical sensor is configured to output an analog signal that is indicative of the concentration of the selected chemical in the surrounding environment.

In one embodiment the chemical sensor includes an electrode formed on the first passivation layer. The exposed portion of the electrode is coated in a reactant configured to react with the selected chemical.

In one embodiment a temperature sensor is formed on the first passivation layer. An opening in the second passivation layer exposes a portion of a heat sensitive resistor to the environment surrounding the integrated circuit die. The heat sensitive resistor is configured to output an analog temperature signal indicative of the temperature of the environment surrounding the integrated circuit die.

In one embodiment a humidity sensor is formed on the first passivation layer. An opening in the second passivation layer exposes a portion of the humidity sensor to the environment surrounding the integrated circuit die. The humidity sensor is configured to output an analog humidity signal indicative of the temperature of the environment surrounding the integrated circuit die.

BRIEF DESCRIPTION OF THE SEVERAL VIEWS OF THE DRAWINGS

FIG. 5B is a top view of a heat sensor according to one embodiment.

DETAILED DESCRIPTION

Figure 1:
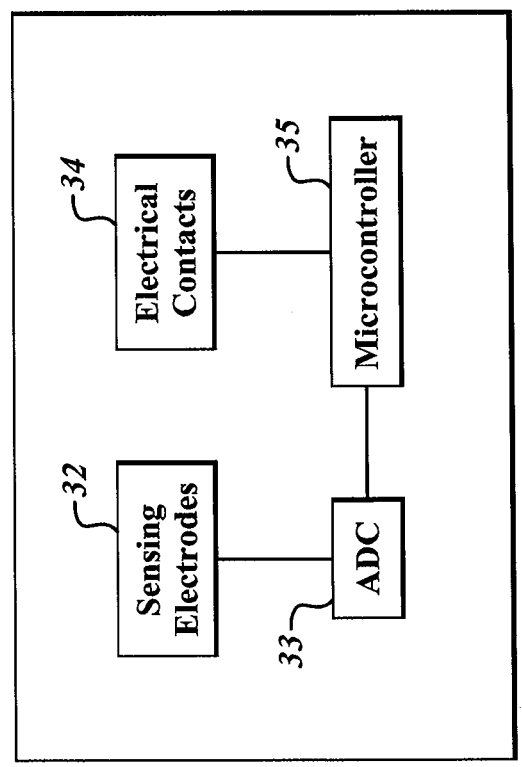
FIG. 1 is a block diagram of a integrated circuit die according to one embodiment.

FIG. 1 illustrates a integrated circuit die 30 according to one embodiment. The integrated circuit die 30 includes sensing electrodes 32 coupled to an analog to digital converter 33. Electrical contacts 34 and the analog to digital converter 33 are coupled to a microcontroller 35.

The sensing electrodes 32 comprise a chemical sensor. The sensing electrodes 32 are configured to sense the presence of a selected chemical. The sensing electrodes 32 output an analog signal representative of the presence of or in some cases the concentration of the selected chemical in the environment surrounding the integrated circuit die 30. The electrical contacts 34 comprise both input and output contacts for the integrated circuit die 30. In one embodiment, the electrical contacts 34 receive the power supply voltages for the integrated circuit die 30. The microcontroller 35 in the integrated circuit die 30 may be accessed via the electrical contacts 34. The integrated circuit die 30 may also output signals through the electrical contacts 34. Electrical contacts 34 may be coupled to a ball grid array, pin grid array, leads of a lead frame, solder balls of an embedded wafer level ball grid array or any other suitable method for interfacing with the integrated circuit die 30.

In one embodiment the sensing electrodes 32 are covered in a reactant which is configured to react with the selected chemical. The reactant chosen is a reactant that will react with the selected chemical in a desired way. The reactant may be an enzyme, a catalyst, a chemical compounds, biological compounds, or any other suitable reactant configured to react with the selected chemical. In one embodiment, when the selected chemical contacts the reactant on the sensing electrodes 32, the sensing electrodes 32 output an analog signal indicative of the concentration of the selected chemical in the environment around the integrated circuit die 30. The analog signal output by the sensing electrodes 32 can be a voltage signal or a current signal.

The integrated circuit die 30 may contain a monocrystaline semiconductor substrate. Transistors may be formed in the monocrystaline silicon substrate. Transistors formed in the monocrystaline silicon substrate form the analog-to-digital converter 33 and the microcontroller 35. In one embodiment a signal amplifier or any other suitable circuitry that may be formed on the integrated circuit die 30. The signal amplifier can amplify the analog signal before sending the amplified analog signal to the analog to digital converter 33. In one embodiment the signal amplifier is potentiostat configured to control the sensing electrodes 32, to convert the analog signal from an analog current signal to an amplified analog voltage signal, and to output the amplified analog voltage signal to the analog to digital converter 33.

The analog signal output by the sensing electrodes 32 is received by the analog-to-digital converter 33. The analog-to-digital converter 33 converts the analog signal to a digital signal. The analog-to-digital converter 33 then outputs the digital signal to the microcontroller 35 which estimates or computes a value of the concentration of the selected chemical based on the digital signal.

In one embodiment, no transistors are formed in the integrated circuit die 30. Instead all amplification, conversion or microprocessing circuitry is formed on a separate integrated circuit die. In one embodiment the analog-to-digital converter 33 and the microcontroller 35 are formed on a separate integrated circuit die. In such an embodiment the analog signal may be output to the analog-to-digital converter through the electrical contacts 34.

The integrated circuit die 30 including chemical sensor 32 may be used in medical applications such as blood glucose detection, cholesterol detection, hemoglobin detection, blood gas detection, detecting cancer markers, detecting electrolytes, detecting DNA or RNA, detecting illegal drugs or any other suitable medical applications. The chemical sensor may also be used in industrial applications. For example, the chemical sensor may be used to detect pH levels, lead, mercury, chromium, cadmium, arsenic, dissolved solids, fluorides, and volatile organic compounds. The chemical sensor may be used in environmental applications. For example, the chemical sensor may detect carbon monoxide in the environment, NO, H2S, HCN, microorganisms, organic compounds, arsenic, or any other suitable environmental applications. The chemical sensor may be used in automotive applications. For example, the chemical sensor may detect chemicals in the exhaust of an automobile. The chemical sensor may detect carbon monoxide, carbon dioxide, nitrous oxide, oxygen levels, or other particulates in the exhaust of the automobile. The chemical sensor may be utilized in a large number of ways and to sense a large number of chemicals not all of which are described here, and such other uses fall within the scope of the present disclosure.

The sensing electrodes 32 and the specific reactant placed on the sensing electrodes 32 can be selected for each specific application. For example, a different reactant may be used on a blood glucose monitor than may be used in a chemical sensor configured to detect carbon dioxide in the environment or in an automobile. For each selected application, a specific reactant or enzyme will be used. The type of reactant used will be selected according to the application. The specific types of reactants will be apparent to those of skill in the art according to the present disclosure.

A chemical sensor formed of the integrated circuit die 30 and the sensing electrodes 32 can be a single use chemical sensor or a reusable chemical sensor according to the application. For example, a chemical sensor configured to detect blood glucose levels may be used only a single time and discarded, whereas a chemical sensor configured to detect radon in a house may be continuously operated or may be operated repeatedly. Many applications and methods of use of the chemical sensor formed from the integrated circuit die 30 and the sensing electrodes 32 will be apparent to those of skill in the art in light of the present disclosure.

Further details regarding the formation of chemical sensors can be found in copending U.S. patent application Ser. Nos. 13/016,086, 13/170,058, and all which are incorporated by reference in their entireties.

Figure 2:
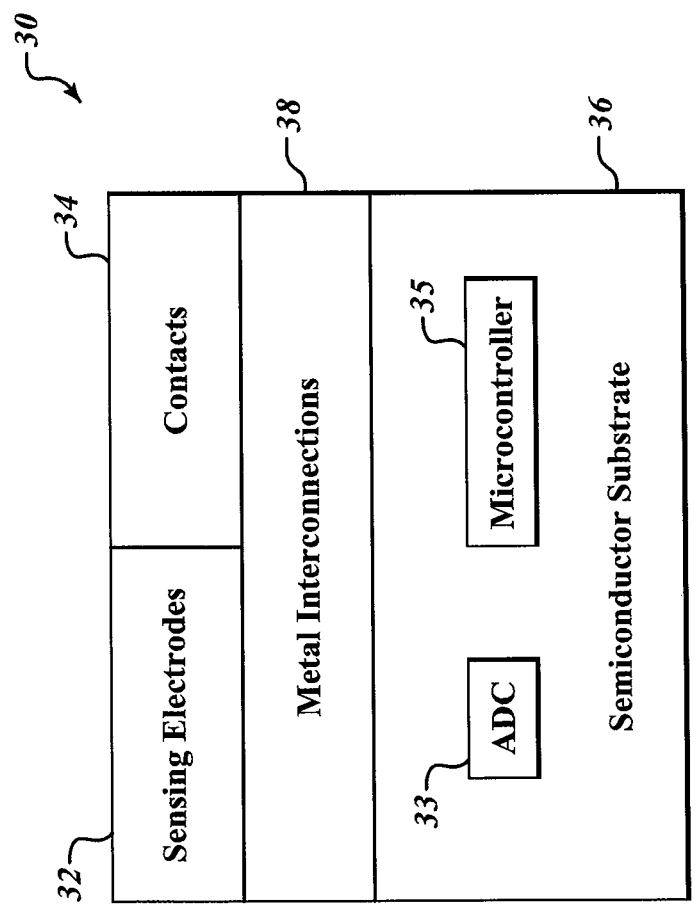
FIG. 2 is a simplified schematic of a cross section of a integrated circuit die according to one embodiment.

FIG. 2 illustrates a schematic of a side view of an integrated circuit die 30 according to one embodiment. The integrated circuit die 30 includes a monocrystalline semiconductor substrate 36. An analog to digital converter 33 and microcontroller 35 are formed in the monocrystalline semiconductor substrate 36. Metal interconnections 38 are formed above the semiconductor substrate 36. Sensing electrodes 32 and contacts 34 are formed above the metal interconnections 38.

In one embodiment, transistors or other circuitry are formed in the semiconductor substrate 36. For example, the analog-to-digital converter 33 and the microcontroller 35 are formed of transistors in the semiconductor substrate utilizing metal interconnections 38. A signal amplifier may also be formed in the semiconductor substrate 36. The signal amplifier may receive the analog signal from the sensing electrodes 32 and may output an amplified analog signal to the analog-to-digital converter 33 also formed in the semiconductor substrate 36. The analog-to-digital converter may then convert the analog signal to a digital signal and output the digital signal to a microcontroller. The metal interconnections 38 connect the analog-to-digital converter 33 to the microcontroller 35. If the microcontroller is formed on a separate integrated circuit die, then the analog-to-digital converter may output the digital signal to the microcontroller through the metal interconnections 38 which connect to the contacts 34. The microcontroller 35 on the separate integrated circuit die may then be connected electrically to the contacts 34 and receive the digital signal. The transistors which form the analog-to-digital converter 33, the microcontroller 35 and the signal amplifier may be formed according to conventional CMOS processes. Such processes will not be described herein as they are well known to those of skill in the art.

Metal interconnections 38 are formed in a dielectric layer above the semiconductor substrate. The metal interconnections 38 include metal tracks, for example of metal layers of metal 1, metal 2 or metal 3. The metal interconnections also include contact vias and plugs connecting the various levels of metal tracks to each other and to the semiconductor substrate 36. The metal interconnections 38 may be formed according to any suitable conventional process. For example, the metal tracks may be formed of aluminum or copper and may be formed on thin barrier layers of titanium or titanium nitride. The vias may also be formed of aluminum or copper with barrier and adhesion layers of titanium or titanium nitride on the walls of the via. Plugs may be filled with tungsten also surrounded by barrier layers or adhesion layers of titanium or titanium nitride. Such metal choices and processes performing the metal interconnections are well known to those of skill in the art and will not be further detailed.

The sensing electrodes 32 are formed above the metal interconnections 38. In one embodiment, the sensing electrodes 32 are formed in a passivation layer above the metal interconnections 38. The sensing electrodes 32 contact the metal interconnections 38 at selected regions in order to facilitate transmitting signals between the sensing electrodes and the semiconductor substrate. In this way, the voltages currents from the sensing electrodes 32 can be monitored, controlled or measured. Sensing electrodes may be formed of gold, platinum or any other suitable material. In one embodiment, there are three sensing electrodes 32, including a reference electrode, a counter electrode, and a working electrode coupled to a potentiostat. The working electrode and the reference electrode may be formed of gold while the counter electrode may be formed of platinum. In other embodiments, other materials may be used. In one embodiment, all of the electrodes 32 are formed of the same metal. In one embodiment, there are only two electrodes 32. In one embodiment, there may be more than three electrodes 32.

The contacts 34 are also formed above the metal interconnections 38. The contacts may be formed simultaneously with the sensing electrodes 32 from the same metal layer. The contacts 34 also contact metal interconnections 38 at selected places to enable input and output of signals and voltages through the electrical contacts 34.

A molding compound may encapsulate the integrated circuit die 30. A portion of the molding compound may then be removed to expose the sensing electrodes 32. The reactant described in relation to FIG. 1 may then be placed on the sensing electrodes 32. In this way, the sensing electrodes 32 are exposed to the environment through the reactant. An adhesive or hardening layer may also be placed in the reactant. The adhesive enables the reactant to bond with the sensing electrodes 32, the molding compound, and the passivation layer below the sensing electrodes so that the reactant may be anchored in place.

Figure 3A:
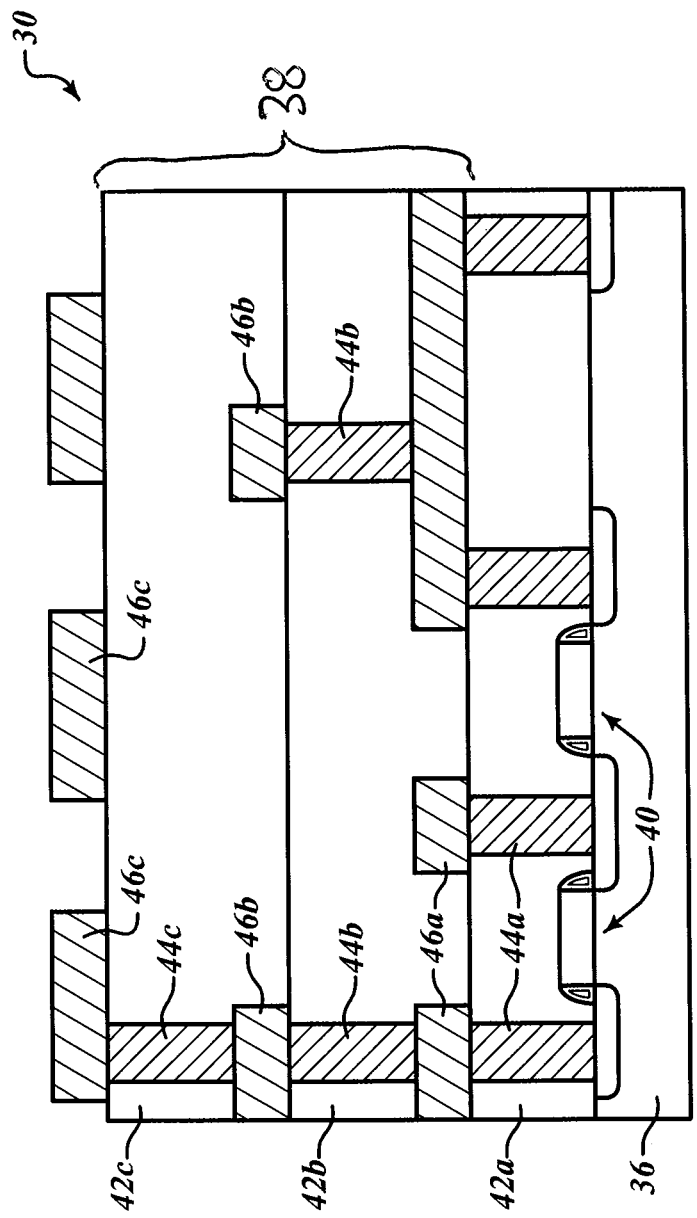
FIGS. 3A-3G are cross sections of a integrated circuit die at an various intermediate stages of manufacture according to one embodiment.

FIG. 3A illustrates a cross section of a integrated circuit die 30 at an intermediate stage of processing. The integrated circuit die 30 includes a monocrystaline silicon substrate 36. Transistors 40 are formed in the monocrystaline silicon substrate 36. The transistors 40 may be formed according to any conventional method for forming transistors in a semiconductor substrate. Such methods are well known to those of skill in the art and will not be detailed here. While two transistors 40 are illustrated in FIG. 3A, it will be understood by those of skill in the art that thousands or millions of transistors may be formed in the monocrystalline silicon substrate 36. The signal amplifier, analog-to-digital converter 33, and microcontroller 35 discussed in relation to FIGS. 1 and 2 may be formed of the transistors 40 in the monocrystalline silicon substrate 36.

Integrated circuit die 30 includes three dielectric layers 42a, 42b, 42c. Dielectric layer 42a is formed directly above the monocrystalline silicon substrate 36. The dielectric layer 42a may comprise a plurality of layers including silicon dioxide layers, silicon nitride layers, spinon glass layers, phosilicate glass layers, or any other suitable dielectric layers used in the formation of integrated circuit die as are known by those of skill in the art.

Contacts 44a are formed in the dielectric layer 42a. The contacts 44a may be formed according to any suitable conventional method. In one example, the contacts 44a are formed of tungsten. Tungsten contact vias may include barrier layers and/or adhesive layers of titanium or titanium nitride. A large variety of materials may be used to form the contacts 44a. Such materials are well known to those of skill in the art and need not be detailed here.

The dielectric layer 42b is formed above the dielectric layer 42a. The dielectric 42b may include the same types of layers found in the dielectric layer 42a. For example, dielectric 42b may include silicon dioxide layers, silicon nitride layers, spin-on glass layers, phosphosilicate glass layers, or any other suitable dielectric layers that may be used in semiconductor processing.

Metal tracks 46a are formed on top of the dielectric layer 42a. The metal tracks 46a are formed of metal 1. In one embodiment, the metal tracks 46a are formed of Al with small amounts of Cu and Si. In other embodiments they are formed of pure Cu or $Al_2Cu$. The metal tracks 46a may also be formed of many other materials, as will be apparent to those of skill of the art in light of the present disclosure. Metal tracks 46a may also include barrier layers or adhesion layers of titanium or titanium nitride. Vias 44b are formed in the dielectric layer 42b and contact metal tracks 46a. Vias 44b may be formed in the same manner as contacts 44a.

Metal tracks 46b are formed on the dielectric layer 42b. Metal tracks 46b are formed of the same material and in substantially the same way as metal tracks 46a. Dielectric layer 42c may be formed of the same materials and in the same manner as dielectric layers 42b and 42a. Vias 44c are formed in the dielectric layer 42c and contact metal tracks 46b. The vias 44c are formed of the same material and in substantially the same manner as contacts and vias 44b and 44a as previously described. Metal tracks 46b are formed of metal 2.

Metal tracks 46c are formed on dielectric layer 42c. Metal tracks 46c are formed of metal 3. Metal tracks 46c are formed in substantially the same manner and of substantially the same materials as metal tracks 46b and 46a.

Figure 3B:
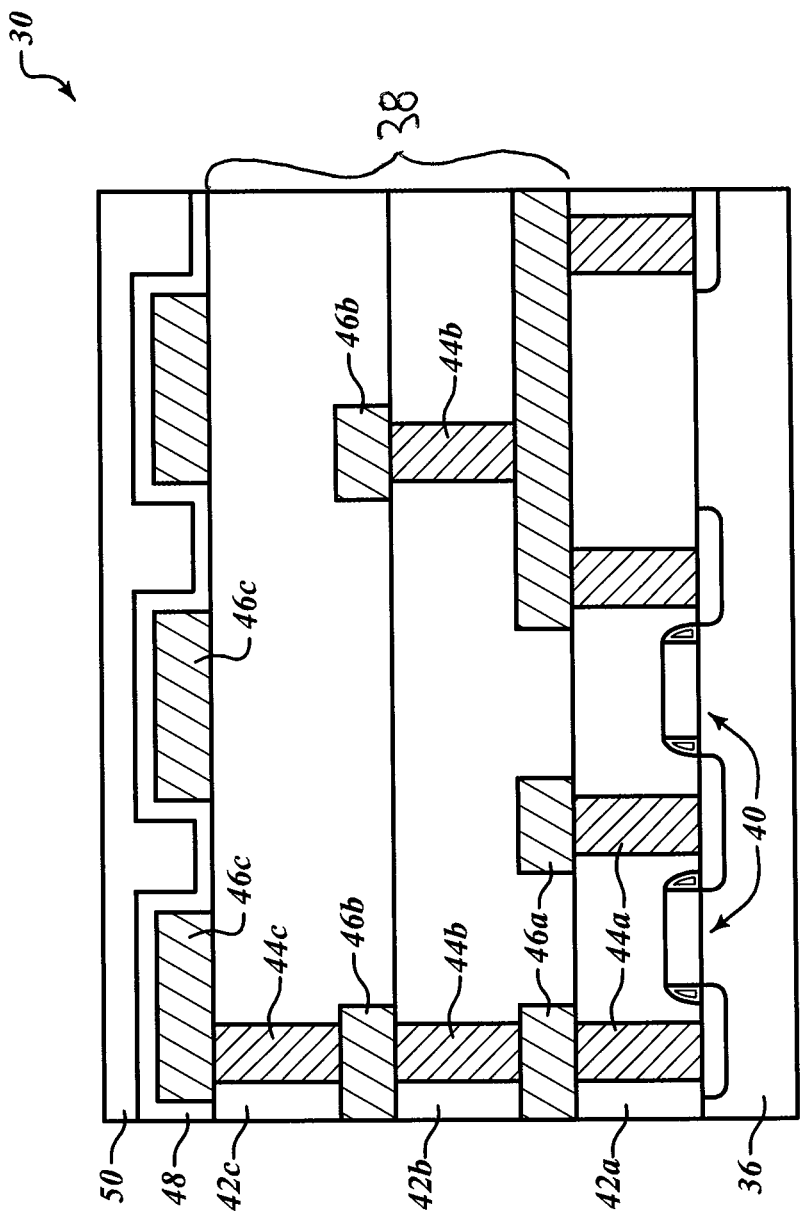

As shown in FIG. 3B, a dielectric layer 48 is formed on metal tracks 46c and dielectric layer 42c. Dielectric layer 48 is a conformal dielectric layer. In one embodiment, the dielectric layer 48 is a phosphosilicate glass. The layer 48 is approximately 5,000 Å thick. Dielectric layer 50 is formed above dielectric layer 48. In one embodiment, dielectric layer 50 is an oxynitride layer. In one embodiment, the oxynitride layer 50 is 16 kÅ thick. The dielectric layer 50 may be a planarizing layer or the dielectric layer 50 may be a conformal layer that has been planarized. The planarization of the dielectric layer 50 may occur by chemical mechanical planarization, or CMP. The dielectric layers 48 and 50 together comprise a passivation layer over the integrated circuit die 30.

Figure 3C:
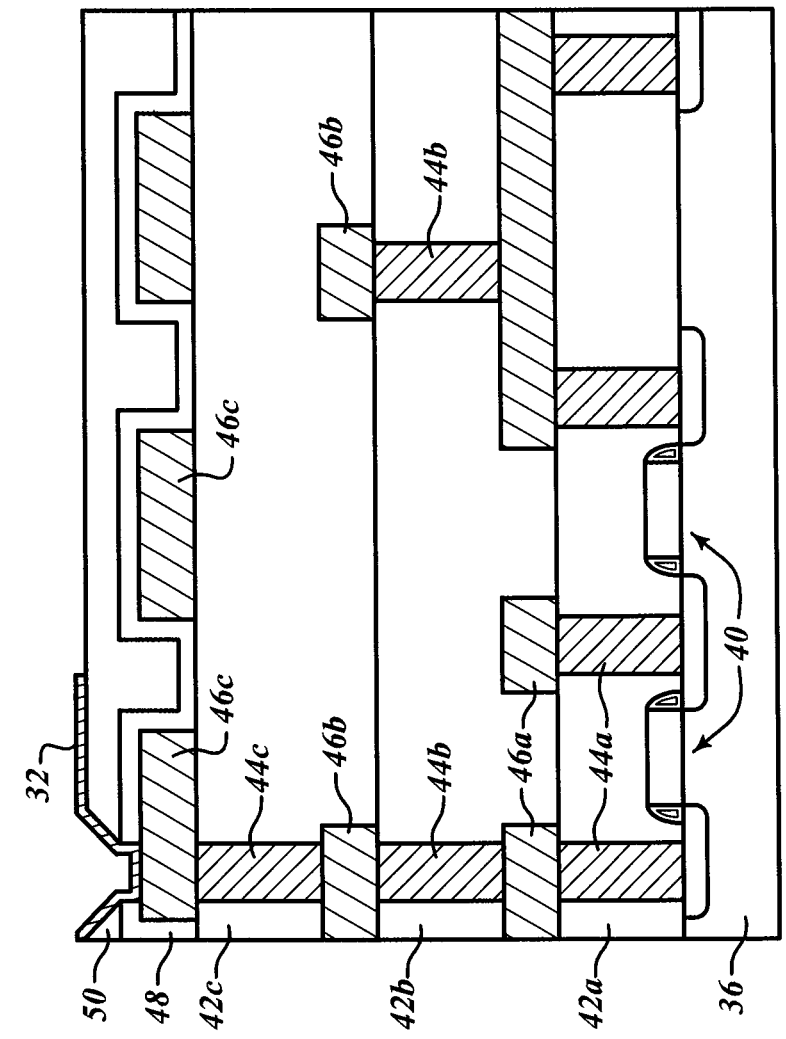

In FIG. 3C, dielectric layer 50 has been etched to open a hole above one of the metal tracks 46c. The dielectric layer 50 may be etched by any suitable process. In one embodiment, the dielectric layer 50 is patterned and etched by conventional photolithographic processes. A layer of platinum is deposited on the dielectric layer 50 and contacts the exposed portion of metal track 46c. The platinum layer is then patterned and etched leaving the electrode 38a shown in FIG. 3C. The electrode 38a is, for example, 2,000 Å thick. In one embodiment, a titanium tungsten barrier layer underlies the platinum layer. The titanium tungsten barrier layer is, for example, 500

Å thick. In one embodiment, the electrode 38a is made of a metal other than platinum, for example, electrode 38a may be formed of gold or of any other suitable metal.

Figure 3D:
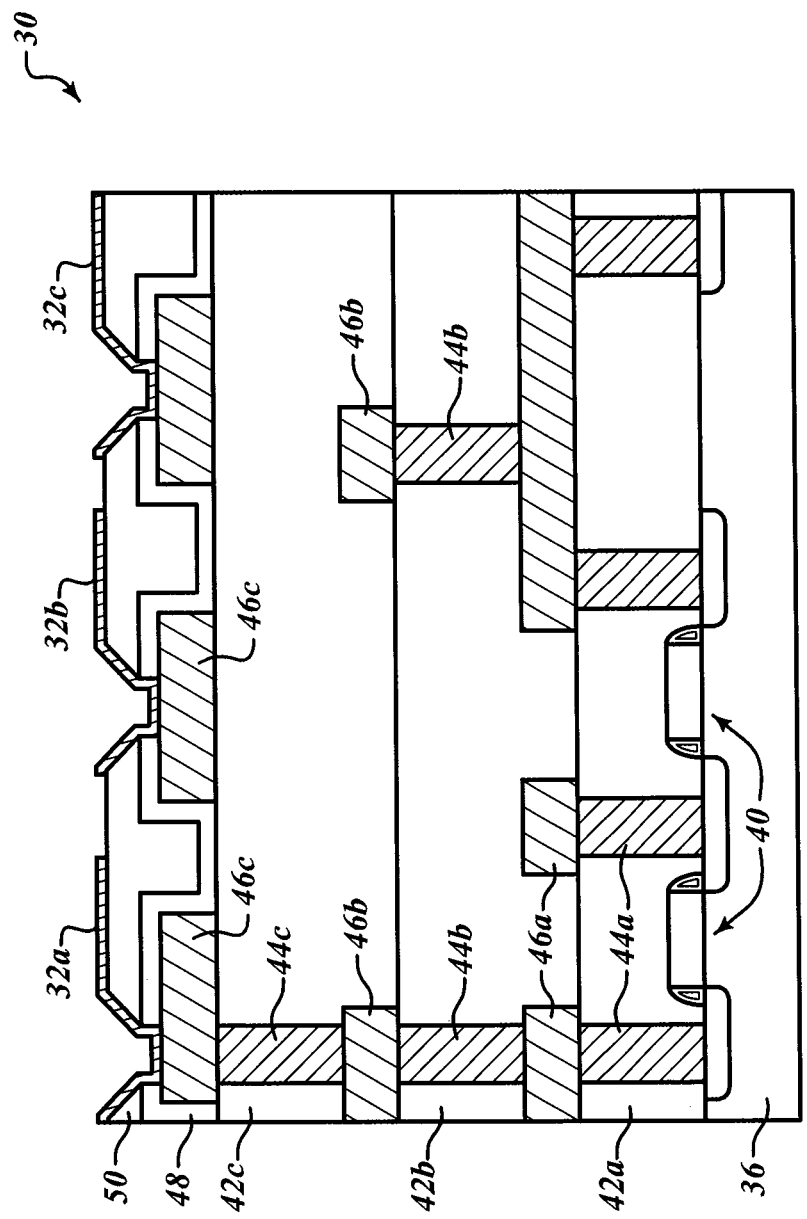

In FIG. 3D, the dielectric layer 50 has been patterned and etched to expose other portions of metal tracks 46c. A thin layer of gold is then deposited on the passivation layer 50 and on the exposed portions of the metal tracks 46c. The gold layer is then patterned and etched, leaving electrodes 32b, 32c in contact with the exposed portions of metal tracks 46c and on passivation layer 50. The electrodes 32b and 32c are 2,000 Å thick. In one embodiment, electrodes 32b and 32c comprise an additional layer of titanium tungsten underlying the gold layer. The titanium tungsten layer is, in one example, 500 Å thick.

Figure 3E:
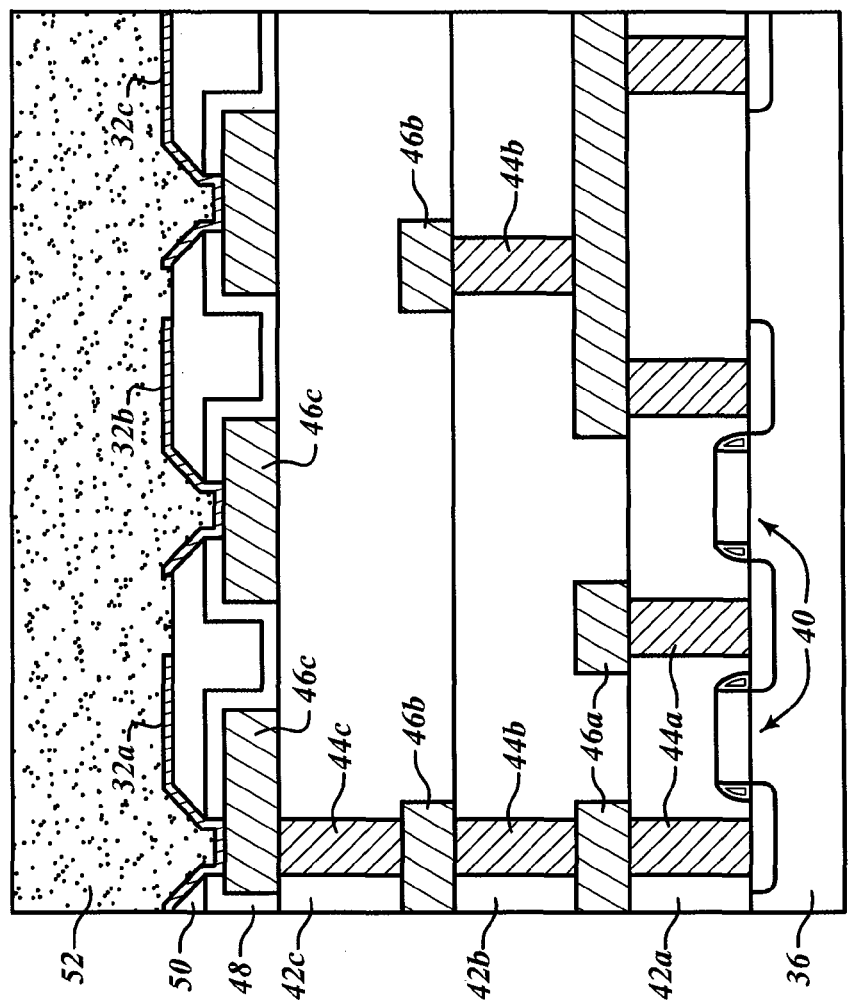
Figure 3F:
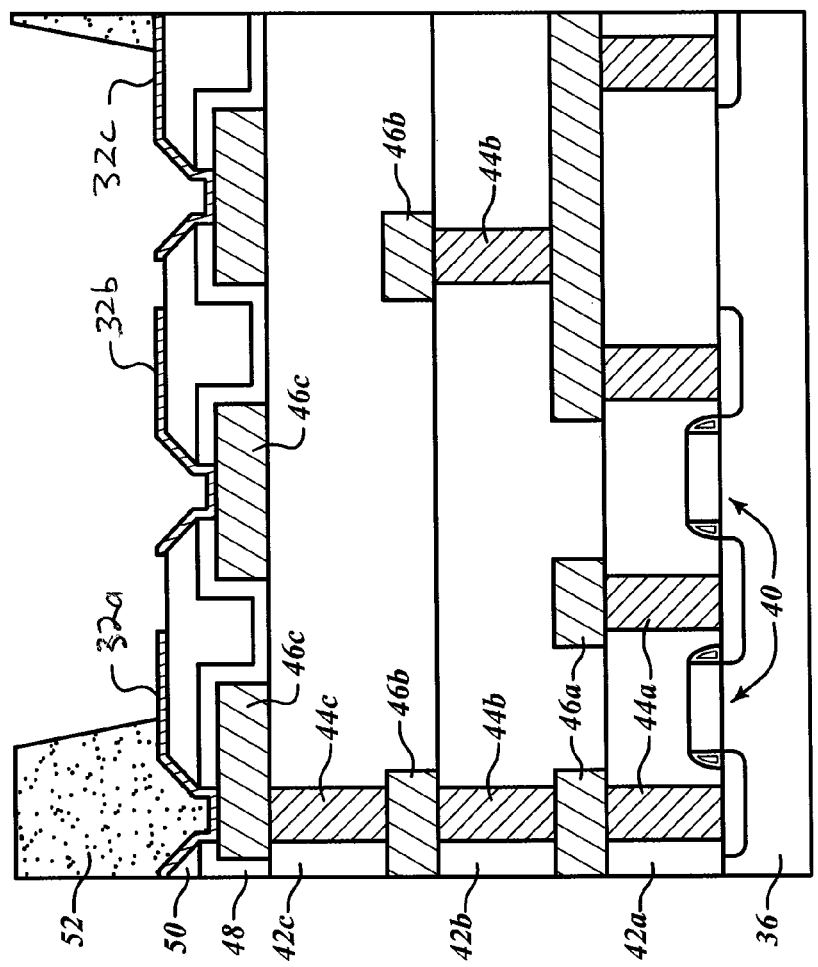

In FIG. 3E, the integrated circuit die 30 has been covered in a passivation layer 52. The passivation layer 52 is, in one example, a molding compound. The molding compound 52 covers the dielectric layer 50 and the electrodes 32a, 32b and 32c. The molding compound is, for example, 9.5 μm thick. The molding compound serves to protect the integrated circuit die 30 from contamination, humidity, and physical damage. Molding compounds are well known to those of skill in the art and are commonly used to encapsulate and package semiconductor dice. The molding compound 52 may be any conventional molding compound or passivation material. The molding compound is then etched to expose the electrodes 32a, 32b, 32c. This leaves the structure shown in FIG. 3F. Molding compound 52 is still present on the integrated circuit die 30, but a selected portion of the molding compound 52 has been removed over the electrodes 32a, 32b, 32c. This opening makes it possible for the electrodes 32a, 32b, 32c to detect the presence of chemicals in the environment surrounding the integrated circuit die 30.

Figure 3G:
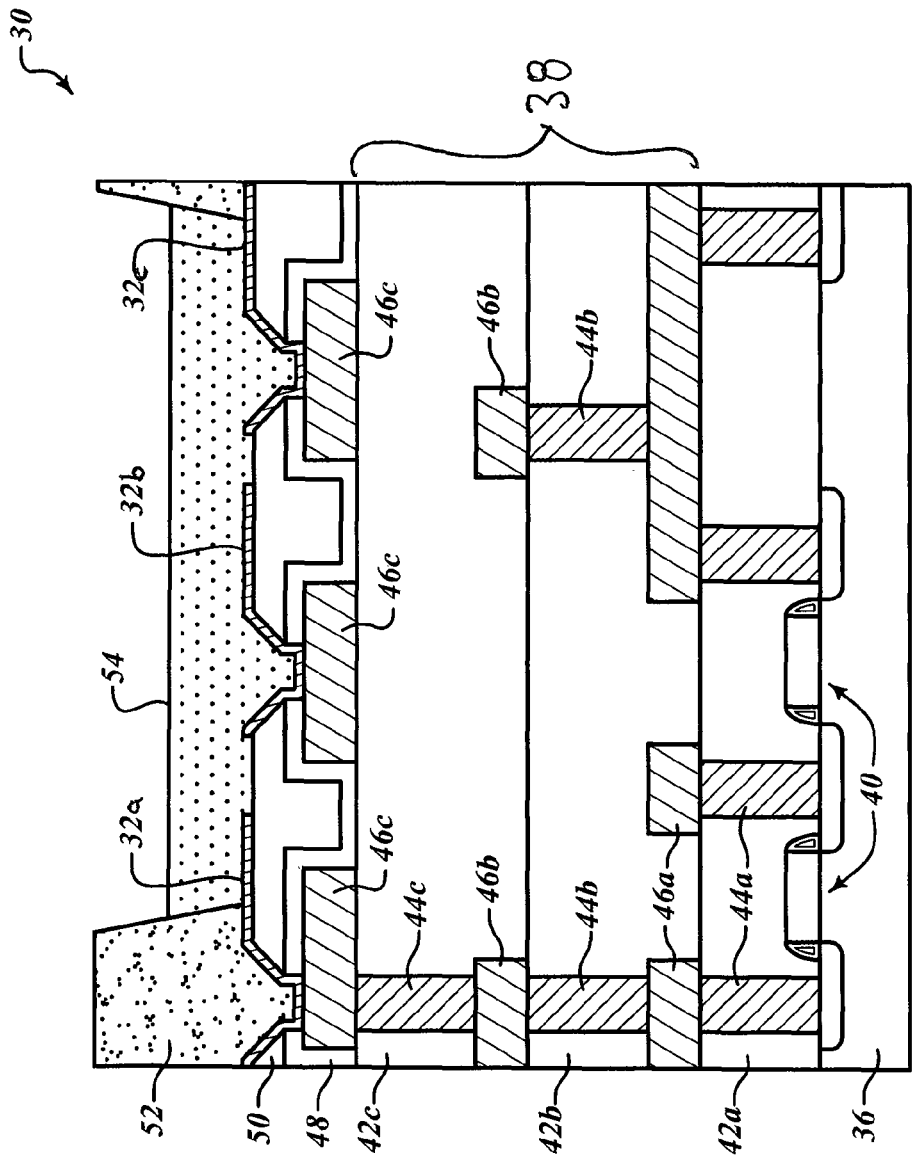

In FIG. 3G, a reactant 54 has been placed in the opening of the molding compound covering the exposed portions of electrodes 32a, 32b, 32c. The reactant 54 is selected according to the desired application of the integrated circuit die 30. The reactant 54 may be an enzyme, a catalyst, a particular compound, or any other suitable substance that may react with the selected chemical.

The reactant 54 electrically connects the electrodes 32a, 32b, 32c. In one embodiment, separate voltages are applied to the electrodes 32a, 32b, 32c. This causes a current to flow between electrodes 32a and 32b. Current will also flow between electrodes 32b and 32c. The reactant 54 acts as an electrical connection between the electrodes 32a, 32b, 32c. When the reactant 54 reacts with the selected chemical in the environment surrounding the integrated circuit die 30, the conductivity of the reactant 54 will increase. Therefore, a higher current will flow between electrodes 32a and 32b as well as electrodes 32b and 32c. The magnitude of the current is indicative of the concentration of the selected chemical in the environment surrounding the integrated circuit die 30. Therefore, if there is a higher concentration of the selected chemical in the environment surrounding the integrated circuit die 30, then a higher current will flow.

In one embodiment, an analog-to-digital converter 33 is formed of transistors 40 and the monocrystalline silicon substrate 36. Electrodes 32a, 32b, 32c are electrically connected to the analog-to-digital converter. The currents generated between the electrodes 32a, 32b, 32c are an analog signal sent to the analog-to-digital converter 33. The analog-to-digital converter 33 converts the analog signal to a digital signal. A microcontroller 35 is also formed of transistors 40 in the monocrystalline silicon substrate 36. The microcontroller 35 receives the digital signal from the analog-to-digital converter 33 and calculates, computes, or estimates a value of the concentration of the selected chemical in the environment surrounding the integrated circuit die 30 based on the digital signal. The microcontroller 35 has stored in memory a calibration curve which correlates a value of the digital signal to a value of the concentration of the selected chemical. The calibration curve is unique to the specific selected chemical and the specific reactant 54 used in the integrated circuit die 30. For each type of reactant 54 that can be used, a different calibration curve will be used in the microcontroller 35. Any type of reactant may be used that is suitable to reacting with the selected chemical in such a way that an analog signal will be generated which is indicative of the value of the concentration of the selected chemical in the environment surrounding the integrated circuit die 30.

In one embodiment, the chemical detector is a carbon monoxide detector. The reactant 54 placed on the electrodes 32a, 32b, and 32c may be an electrolyte that is sensitive to carbon monoxide. In one example, the reactant 54 is sulfuric acid. In the presence of carbon monoxide, the sulfuric acid will allow a greater current to flow between the electrodes 32a and 32b or 32b and 32c. This is an example of an electrochemical reaction in which a chemical reaction in the reactant 54 caused by the presence of carbon monoxide causes an increase in electrical conductivity. This in turn allows a greater current to flow through the reactant 54 between the electrodes 32a, 32b, 32c.

The integrated circuit die 30 can include a chemical sensor that is structured differently than shown in the Figures. For example, the transduction that occurred in the reactant 54 when in the presence of the selected chemical can be other than an electrical transduction. The signal generated need not be a current or a voltage signal but instead can be an optical signal, a capacitive signal, a frequency signal, or any other suitable signal. In one embodiment, the chemical sensor is a carbon monoxide sensor in which the reactant is cyclodextrins or chromophore. In the presence of carbon monoxide, a change in the cyclodextrins or chromophore can be detected by a photodiode in the integrated circuit die with an infrared source. In such an embodiment, rather than having electrodes 32a, 32b, or 32c, the photodiode can be provided adjacent the reactant 54 near a top of the integrated circuit die 30 as well as the infrared emitter to irradiate the reactant 54.

In one embodiment, the integrated circuit die 30 is a blood glucose sensor. The reactant 54 in the embodiment of a blood glucose sensor can be a glucose oxidase enzyme. The glucose oxidase enzyme is sensitive to blood glucose. A current or a voltage between the electrodes 32a and 32b or 32b and 32c can increase or decrease depending on a concentration of blood glucose in contact with the glucose oxidase enzyme 54.

In one embodiment, the integrated circuit die 30 is configured to detect arsenic. In such an embodiment the reactant 54 includes gold nanoparticles and selected organic compounds. The special organic compounds act as arsenic ligands. By utilizing dynamic light scattering, a concentration of arsenic can be detected by the change in structure between the organic compounds and the gold nanoparticles. The integrated circuit die 30 can implement many other reactants 54 and sensor structures suitable to detecting different kinds of chemicals according to principles of the present disclosure. All such different kinds of reactants and structures including chemical reactants, optical reactants, electrical transducers, optical transducers, capacitive transducers, and any other kind of transducers with any suitable structure that can be formed in the integrated circuit die, fall within the scope of the present disclosure. For example, the reactant 54 can include biological cells, antibodies, enzymes, DNA or RNA sequences, or other customized molecules.

In one embodiment, a hardening agent is placed in the reactant 54 to anchor the reactant 54 to the electrodes 32a, 32b, and 32c, as well as to the passivation layer 50. The hardening agent can mix with the reactant 54 or can form a thin film near the bottom of the reactant 54 or can act in any other suitable manner to help adhere the reactant 54 to the electrodes 32a, 32b, and 32c, the passivation layer 50, and the molding compound 52.

While the integrated circuit die 30 used as a chemical sensor has been described as detecting the concentration of a selected chemical in an environment surrounding the integrated circuit die 30, integrated circuit die 30 can be configured to merely detect the presence of the selected chemical in the environment surrounding the integrated circuit die 30. In one embodiment, the integrated circuit die 30 is configured to simply detect whether the selected chemical exceeds a threshold concentration in the environment surrounding the integrated circuit die 30. In one embodiment, the integrated circuit die 30 can output a signal indicating, in any suitable manner, a concentration of the selected chemical. The concentration can be output in parts per million, in percentage, or in any other suitable manner.

The integrated circuit die 30 can also be configured to merely detect the presence of the selected chemical output a simple yes or no type signal. In such an embodiment, the integrated circuit die 30 outputs a low signal when the concentration of the selected chemical is below a selected threshold and can output a high signal when the concentration of the selected chemical in the environment surrounding the integrated circuit die 30 has exceeded the selected threshold. Many other detection schemes are possible and fall within the scope of the present disclosure.

The integrated circuit die 30 can include a chemical sensor that is a single-use chemical sensor or a reusable chemical sensor or a continuously used chemical sensor. In one embodiment the integrated circuit die 30 is a radon detector which is in continuous use. The integrated circuit die 30 can be placed in the basement of a home or other building and continuously monitor the presence of radon. In one embodiment the chemical sensor can be a single use chemical sensor such as in a blood glucose sensor. In other embodiments the integrated circuit die 30 can be activated multiple times to detect the selected chemical.

Figure 4:
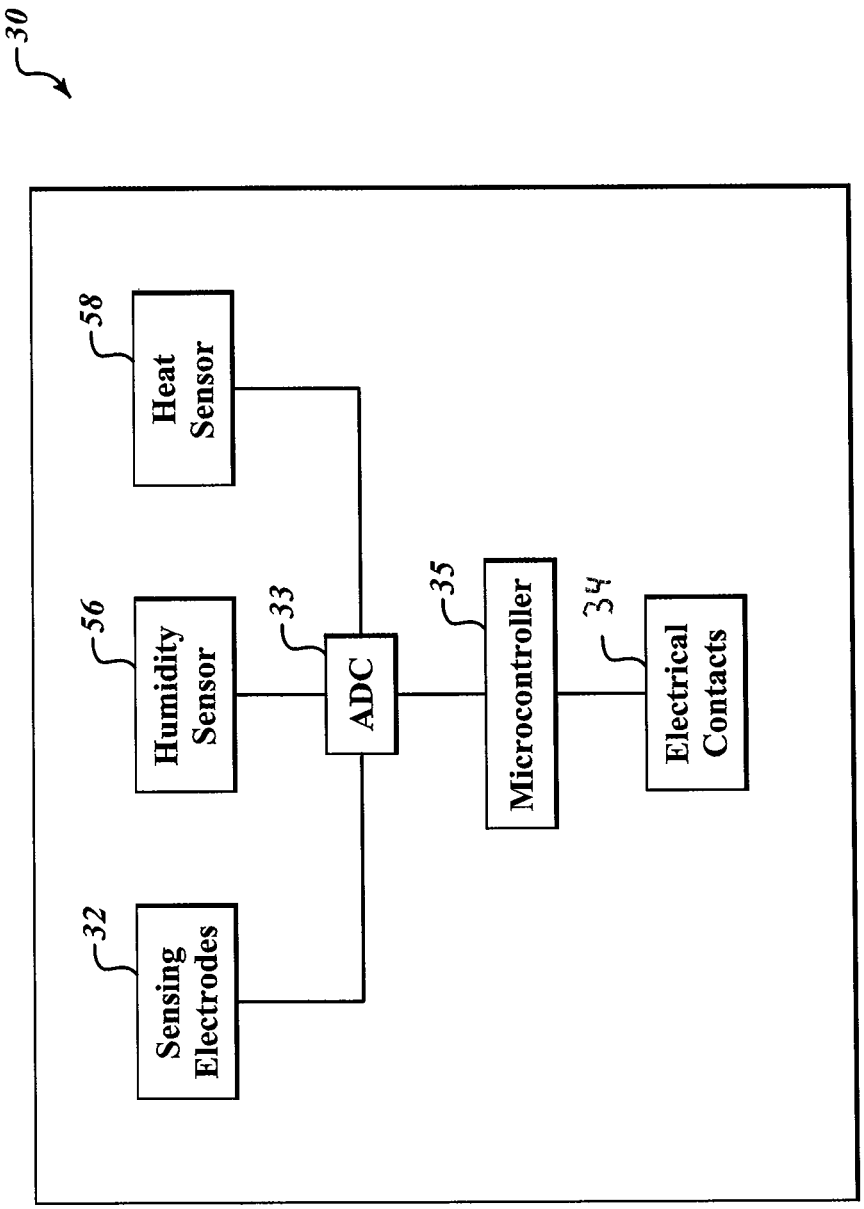
FIG. 4 is a block diagram of a integrated circuit die including a humidity sensor and a heat sensor according to one embodiment.

FIG. 4 is a block diagram of a integrated circuit die 30 according to one embodiment. The integrated circuit die 30 includes sensing electrodes 32, a humidity sensor 56, and a heat sensor 58, each connected to an analog-to-digital converter 33. The analog-to-digital converter 33 is connected to the microcontroller 35. The microcontroller 35 is connected to electrical contacts 34.

Depending on the chemical being sensed, the analog signal output by the sensing electrodes 32 may vary according to the humidity and the temperature in the surrounding environment. Thus, the analog signal output by the sensing electrodes 32 may be based in part on the humidity and heat and not just the concentration of the selected chemical. If the humidity and the heat in the surrounding environment are not taken into account, an erroneous value of the concentration of the selected chemical can be computed. For this reason, in one embodiment the integrated circuit die 30 includes the humidity sensor 56 and the heat sensor 58. The humidity sensor 56 detects the humidity in the surrounding environment. The humidity sensor 56 outputs an analog humidity signal to the analog-to-digital converter 33. The heat sensor 58 is configured to sense the temperature in the surrounding environment. The heat sensor 58 outputs an analog temperature signal to the analog-to-digital converter 33. The analog-to-digital converter 33 converts the analog signal from the sensing electrodes to a digital signal. The analog-to-digital converter 33 also converts the analog humidity signal to a digital humidity signal and converts the analog temperature signal to a digital temperature signal. The analog-to-digital converter 33 then outputs the digital signal, the digital humidity signal, and the digital temperature signal to the microcontroller 35.

The microcontroller 35 then calculates a value of the concentration of the selected chemical and its surrounding environment based on the digital signal, the digital humidity signal, and the digital temperature signal. The microcontroller 35 has stored in memory a calibration table which correlates values of the digital signal, the digital humidity signal and the digital heat signal to values of a concentration of the selected chemical. The microcontroller 35 can then output the value of the concentration of the selected chemical through the electrical contacts 34.

Figure 5A:
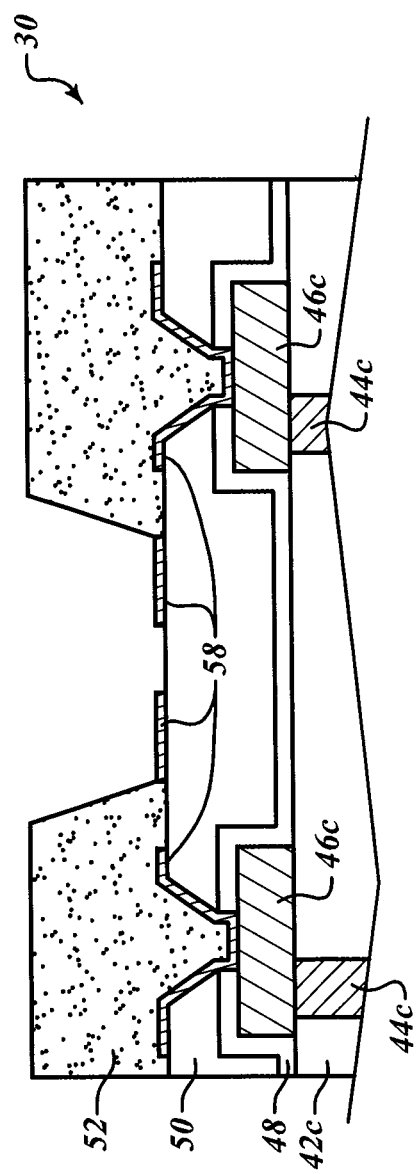
FIG. 5A is a cross section of a integrated circuit die including a heat sensor according to one embodiment.

FIG. 5A is a cross section of a integrated circuit die 30 according to one embodiment. The integrated circuit die 30 includes a temperature sensor 58. The temperature sensor 58 is a temperature sensitive resistor. The temperature sensitive resistor 58 is made from a thin layer of platinum, approximately 2,000 Å thick. The platinum layer from which the temperature sensitive resistor 58 is formed is the same platinum layer from which the electrode 32a is formed in FIG. 3C. Therefore, when the platinum layer is patterned to form the electrode 32a in FIG. 3C, the platinum layer is also patterned to form the resistor 58. Passivation layers 50 and 48 have been previously etched to expose portions of metal tracks 46C on which the platinum layer is then formed. The molding compound 52 is etched to expose portions of the resistor 58. The resistor 58 is thus exposed to the surrounding environment and the temperature of the resistor can freely change based on the temperature of the surrounding environment.

A current signal is passed through the resistor 58 from metal tracks 46c. A voltage is supplied between the two metal tracks 46c shown in FIG. 5A. This causes a current to flow through the heat sensitive resistor 58. The resistance of the resistor 58 varies according to the temperature of the resistor 58. If the temperature of the environment surrounding the integrated circuit die 30 is high, then the temperature of the exposed portions of the heat sensitive resistor 58 will also be very high. This high temperature will change the resistance of the heat sensitive resistor 58, and the current flowing through the heat sensitive resistor 58 will change as well. This current signal can be changed to an analog voltage temperature signal by appropriate circuitry which can be formed in the monocrystalline silicon substrate 36 of the integrated circuit die 30. This analog temperature signal can then be output to the analog-to-digital converter 33. The analog-to-digital converter 33 can convert the analog temperature signal to a digital temperature signal. The digital temperature signal can then be output to a microcontroller 35. The microcontroller 35 can then take into account the digital temperature signal when computing or estimating the value of the concentration of the selected chemical in the environment surroundings of the integrated circuit die 30.

FIG. 5B is a top view of the heat sensitive resistor 58 of FIG. 5A. Portions of the heat sensitive resistor 58 are exposed through an opening 60 in the passivation layer 52. In practice, the heat sensitive resistor 58 may be much longer than shown in FIG. 5B. The heat sensitive resistor 58 may also be formed in a material other than platinum. The heat sensitive resistor 58 may include an adhesion layer of titanium tungsten 500 Å thick. The adhesion layer promotes adhesion of the heat sensitive resistor 58 to the passivation layer and the metal tracks

46c. The exposed portion of the heat sensitive resistor 58 will reach the temperature of the surrounding environment, or nearly so. The resistance of the exposed portions of the resistor 58 will therefore change. This changes the total resistance of the resistor 58. When a voltage is applied across the resistor 58, a current will flow based on the resistance of the resistor 58. If the resistance has been altered based on a change in the temperature, then the current flowing through the resistor 58 will also change.

Figure 6:
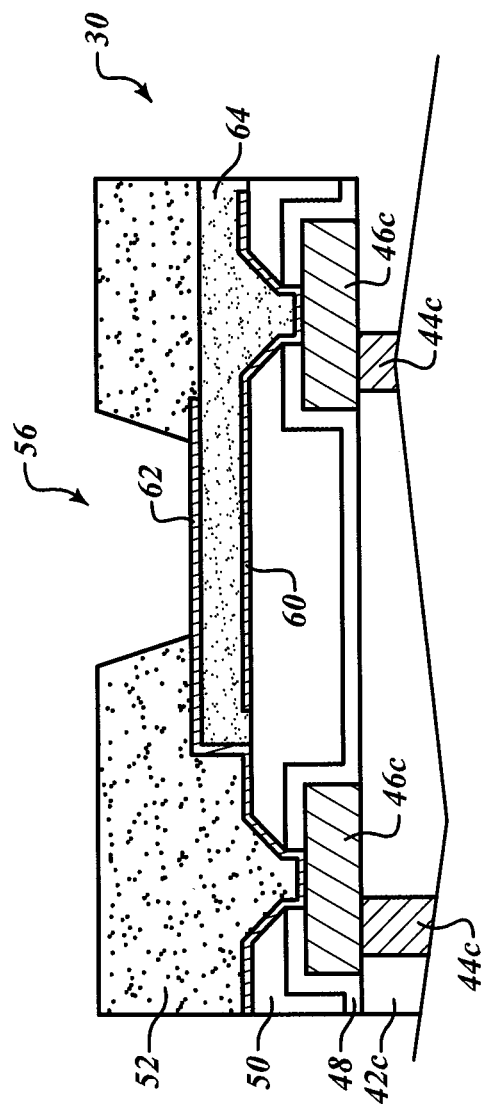
FIG. 6 is a cross section of a integrated circuit die including a humidity sensor according to one embodiment.

FIG. 6 illustrates a integrated circuit die 30 according to one embodiment. A humidity sensor 56 has been formed in the integrated circuit die 30. The humidity sensor 56 includes a bottom electrode 60, a top electrode 62, and a humidity sensitive layer 64 separating the top electrode 62 from the bottom electrode 60. The bottom electrode 60 is formed from the same platinum layer that forms the heat sensitive resistor 58 and the sensing electrode 32a. The top electrode 62 is formed from the same gold layer that forms electrodes 32b and 32c. The humidity sensitive layer 64 is formed after formation of the bottom electrode 60 and before formation of the top electrode 62. Therefore, after the bottom electrode 60 has been patterned and etched the humidity sensitive layer 64 is deposited on the surface of the bottom electrode 60 and passivation layer 50. In one embodiment, the humidity sensitive layer 64 is 5,000 Å thick and comprises polyimide. In one embodiment the humidity sensitive layer 64 is a humidity sensitive dielectric layer wherein a dielectric constant of the humidity sensitive layer 64 varies according to the humidity in the surrounding environment. In one embodiment, the dielectric constant of the humidity sensitive dielectric layer 64 is about 2.2 when there is no humidity. The dielectric constant of the dielectric layer 64 is about 3.2 when there is 100% humidity. The electrodes 60 and 62 form two plates of a humidity sensitive capacitor 56. However, alternatively, the humidity sensitive layer 64 may be of a material having a resistance which varies according to the humidity, or the humidity sensitive layer 64 may include any suitable material that is sensitive to the humidity.

The humidity sensitive layer 64 is patterned and etched so that a portion of the humidity sensitive layer 64 remains on the bottom electrode 60 as well as on portions of the passivation layer 50. After the humidity sensitive layer has been patterned and etched, a gold layer is deposited on the passivation layer 50 on exposed portions of the electrical tracks 56 and on the humidity sensitive layer 64. The gold layer is then patterned and etched to form top electrode 62. The gold layer is the same gold layer that forms electrodes 32b and 32c.

Bottom electrode 60, humidity sensitive humidity sensitive layer 64, and electrode 62 form the humidity sensitive capacitor 56. Molding compound 52 is then deposited on the integrated circuit die 30. The molding compound 52 is opened to expose the top plate 62 of the humidity sensitive capacitor 56. The top plate 62 may also be patterned and etched so that there are holes opened in the top plate 62 to expose portions of the humidity sensitive humidity sensitive layer 64. This allows humidity to enter into the humidity sensitive humidity sensitive layer 64 through openings in the top electrode 62. A voltage is applied between the top electrode 62 and the bottom electrode 60, the electrical tracks 46c. As the humidity in the surrounding environment changes, the dielectric constant of the humidity sensitive layer 64 will also vary. This variation in the dielectric constant of the humidity sensitive layer 64 will cause the capacitance of the humidity sensitive capacitor 56 to vary as well. This changing capacitance can be converted to an analog humidity signal through appropriate circuitry formed in the monocrystalline silicon semiconductor layer 36. The analog humidity signal can then be output to the analog-to-digital converter 33. The analog-to-digital converter 33 can then convert the analog humidity signal to a digital humidity signal. The analog-to-digital converter 33 can then output the digital humidity signal to the microcontroller 35. The microcontroller 35 can then take into account the digital humidity signal when calculating the value of the concentration of the selected chemical in the environment surrounding the integrated circuit die 30.

Figure 7:
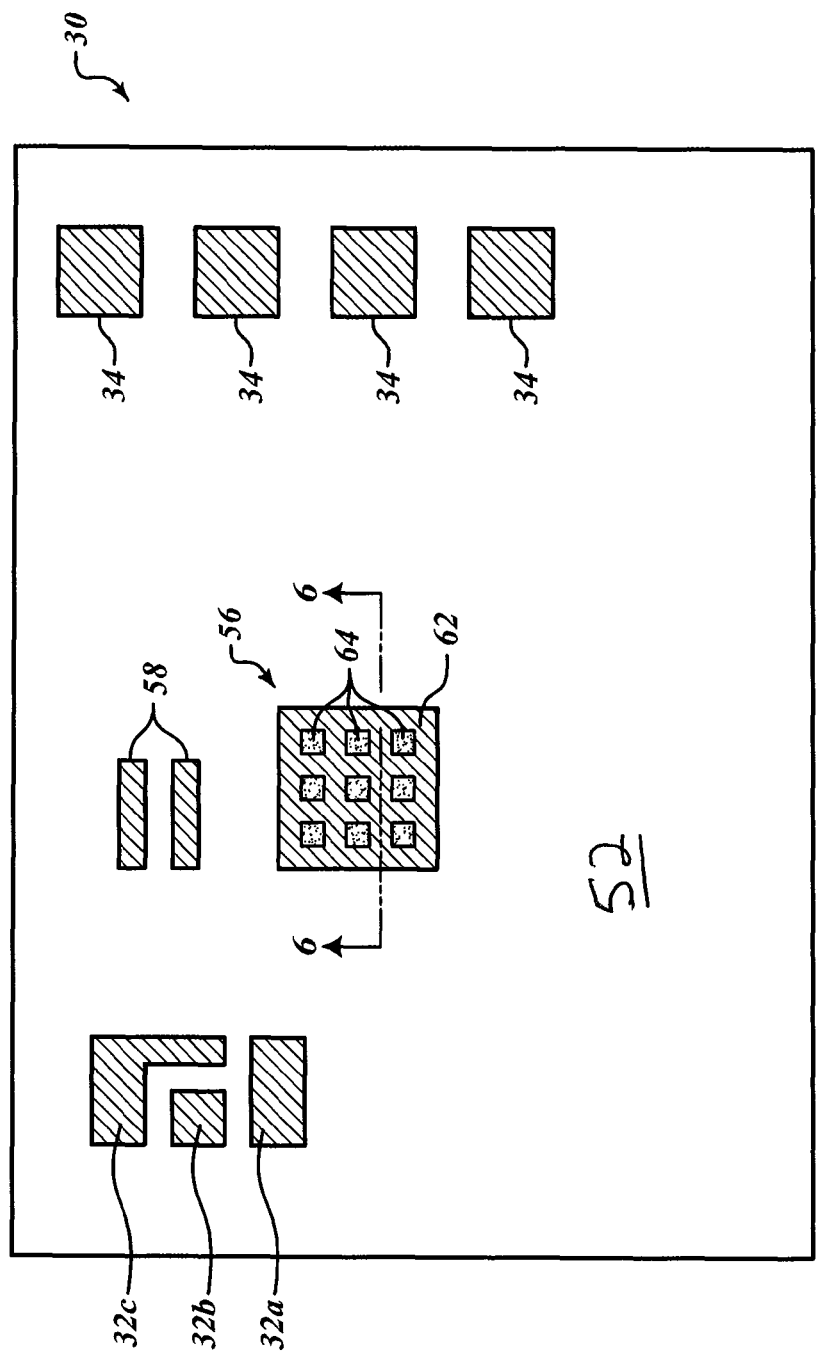
FIG. 7 is a top view of a integrated circuit die according to one embodiment.

FIG. 7 is a top view of a integrated circuit die 30 according to one embodiment. The integrated circuit die 30 is covered in molding compound 52 as described previously. The molding compound 52 has been opened to expose electrodes 32a, 32b, and 32c of the chemical sensor 32. The molding compound 52 has also been opened to expose portions of the heat sensitive resistor 58. The molding compound 52 has also been opened to expose the top plate 62 of the humidity sensitive capacitor 56. The molding compound 52 has also been opened to expose electrical contacts 34 of the integrated circuit die 30. The electrodes 32a, 32b, and 32c are coated in the reactant 54 as described previously. The electrodes 32a, 32b, and 32c generate the analog signal which varies according to the concentration of the selected chemical in the environment surrounding the integrated circuit die 30. The temperature of the exposed portions of the heat sensitive resistor 58 will change according to the temperature of the surrounding environment. As the temperature of the exposed portions of the heat sensitive resistor 58 changes, the resistance of the heat sensitive resistor 58 will also change. An analog temperature signal has an output from the heat sensitive resistor 58 to the analog-to-digital converter.

The top plate 62 of the humidity sensitive capacitor 56 is exposed to the surrounding environment. The top electrode 62 of the humidity sensitive capacitor 56 has been etched to expose portions of the humidity sensitive dielectric layer 64. These openings allow humidity to enter the humidity sensitive layer 64 through the top electrode 62. The dielectric constant of the humidity sensitive dielectric layer 64 changes according to the humidity of the surrounding environment. This change in the dielectric constant of the dielectric layer 64 also changes the analog humidity signal output from the capacitor 56. The analog-to-digital converter 33 can then convert the analog humidity signal to a digital humidity signal. The microcontroller 35 can then take into account the digital humidity signal when calculating the value of the concentration of the selected chemical in the environment surrounding the integrated circuit die.

Figure 8:
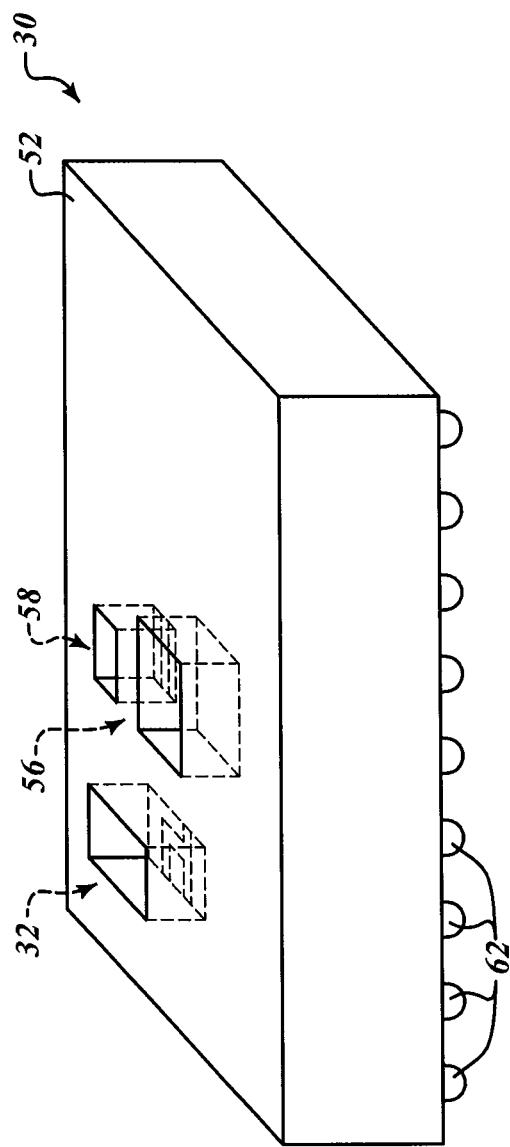
FIG. 8 is an elevated perspective view of a packaged integrated circuit die including a ball grid array according to one embodiment.

FIG. 8 illustrates a packaged integrated circuit die 30 according to one embodiment. The packaged integrated circuit die 30 is encapsulated in molding compound 52. The molding compound has been removed in selected places to expose electrodes 32a, 32b, 32c in a first opening, the heat sensor 58 in a second opening, and the humidity sensor 56 in a third opening. Solder balls 62 are electrical contacts which can electrically connect the integrated circuit die 30 in a device or system.

Figure 9:
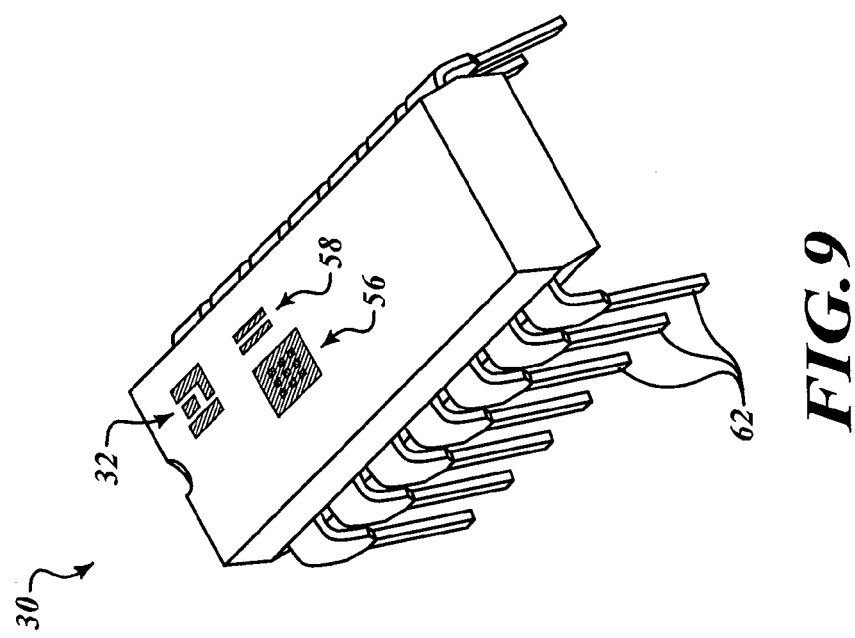
FIG. 9 is an elevated perspective view of a packaged integrated circuit die including a lead frame according to one embodiment.

FIG. 9 illustrates a packaged integrated circuit die 30 according to one embodiment. The electrodes 32a, 32b, and 32c are exposed to the surrounding environment. The heat sensor 58, and humidity sensor 56 are also connected to the surrounding environment. Leads 62 of the packaged integrated circuit die 30 are electrical contacts which can electrically connect the integrated circuit die 30 in a device or system.

Figure 10:
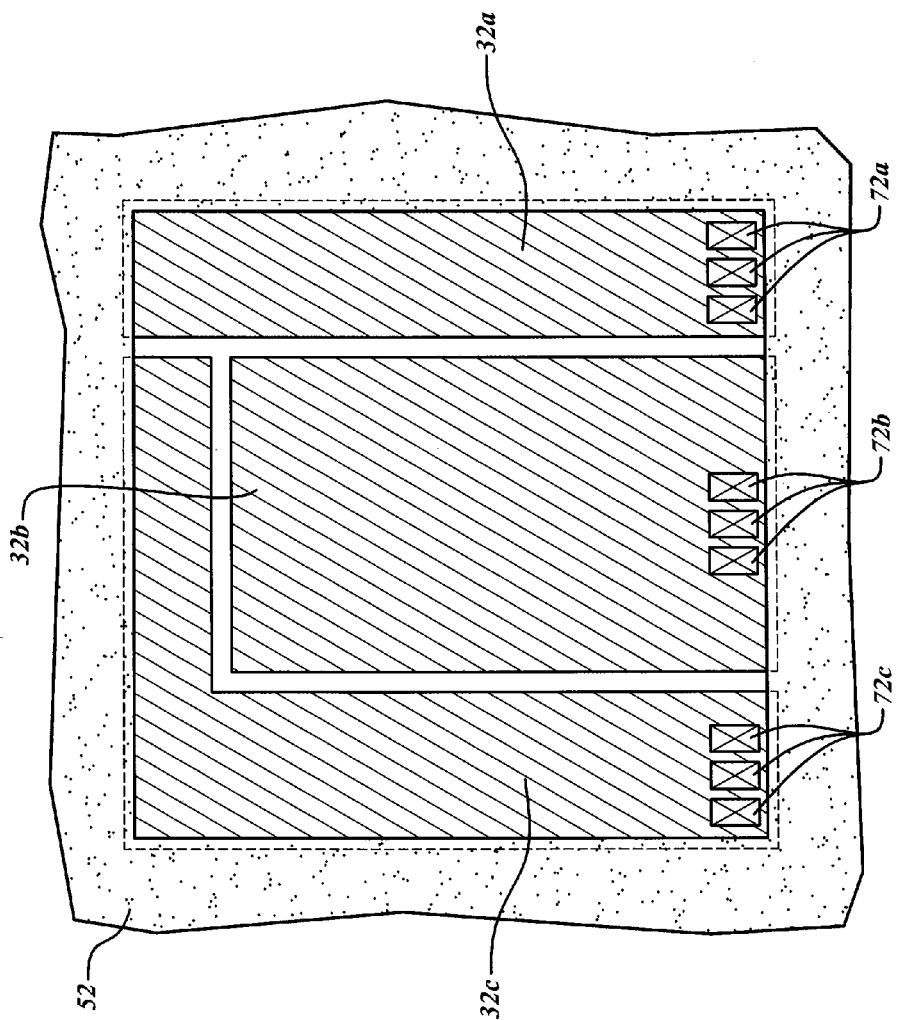
FIG. 10 is a top view of sensor electrodes according to one embodiment.

FIG. 10 illustrates a top view of chemical sensor electrodes 32a, 32b, and 32c according to one embodiment. The integrated circuit die 30 is covered in molding compound 52 as described previously. The molding compound has been removed in a selected location to expose the electrodes 32a, 32b, and 32c. A reactant 54 coats the electrodes 32a, 32b, and 32c, as described previously. However, the reactant 54 is not shown in FIG. 10. In one embodiment, the electrodes 32a, 32b, and 32c are controlled by a potentiostat circuit formed in the integrated circuit die. The potentiostat controls the voltages applied to the electrodes 32a, 32b, and 32c. In the presence of the reactant 54, a current flows between electrodes 32b and 32c and between electrodes 32a and 32b. The currents flowing between the electrodes depend in part on the concentration of the selected chemical in the environment surrounding the integrated circuit die 30. Contacts 72a, 72b, and 72c electrically connect the electrodes 32a, 32b, and 32c, respectively, to electrical connections 46 below the electrodes 32a, 32b, and 32c. The metal interconnections 46 are not shown in FIG. 10. In one embodiment, electrode 32a is a reference electrode, electrode 32b is a working electrode, and electrode 32c is a counter electrode. The counter electrode 32c is made from a different material than the working electrode 32b and the reference electrode 32a. In one embodiment, the working electrode 32b and the reference electrode 32a are made of gold. The counter electrode 32c is made of platinum. Other suitable metals and configurations for the electrodes 32a, 32b, and 32c can be used and fall within the scope of the present disclosure.

The gap separating the electrode 32a from the electrode 32b is about 20 μm. The gap separating the electrode 32a from the electrode 32c is also about 20 μm. The gap separating the electrode 32b from the electrode 32c is about 20 μm. Other distances between the electrodes 32a, 32b, and 32c as well as shapes of the electrodes are possible and fall within the scope of the present disclosure. In one embodiment, the contacts 72a, 72b, and 72c are each 10 microns by 10 microns. In one embodiment, the integrated circuit die 30 has five metal layers. Metal layer 4 includes a platinum layer from which electrode 32c has been formed. Metal layer 5 is a gold metal layer from which electrodes 32a and 32b are formed. Metal layer 3 is in the layer below metal layers 4 and 5. Metal interconnections 46 are formed in the third metal layer as described previously. The contacts 72a, 72b, and 72c electrically connect the electrodes 32a, 32b, and 32c to the metal interconnections 46.

Figure 11:
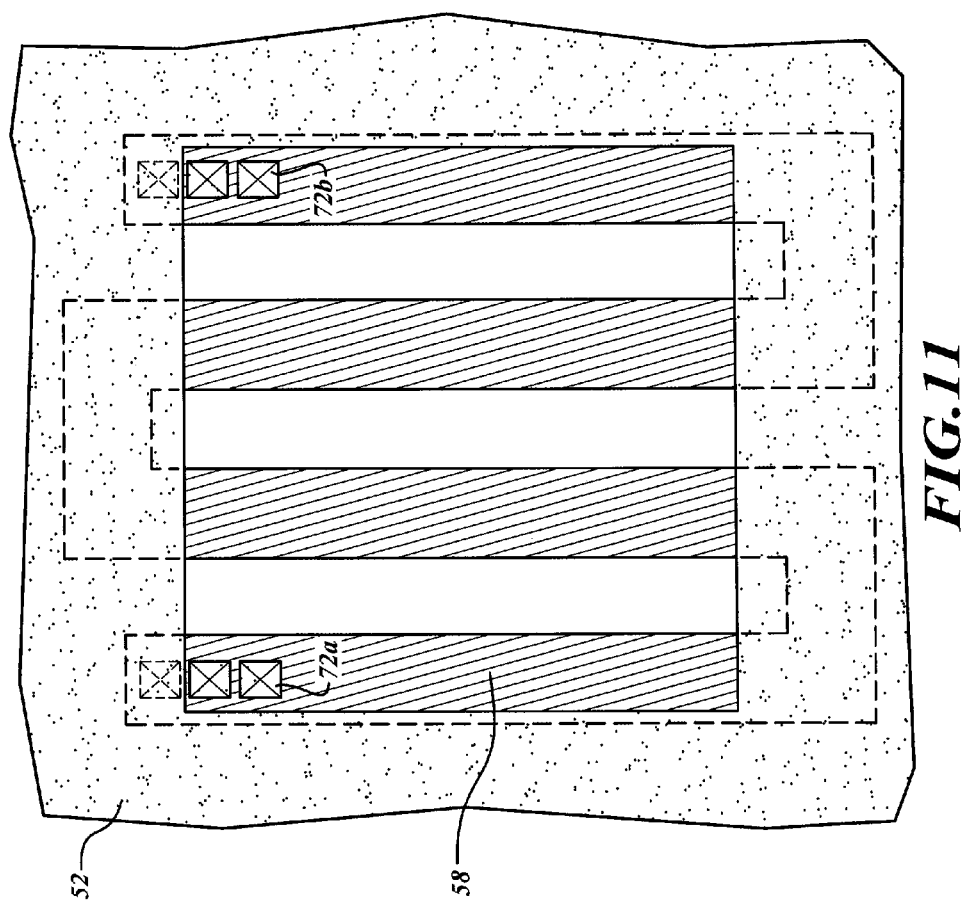
FIG. 11 is a top view of a thermal sensor according to one embodiment.

FIG. 11 illustrates a thermal sensor 58. The thermal sensor 58 is a resistor 58 whose resistivity varies with temperature. The molding compound 52 which covers the integrated circuit die 30 has been opened to expose a portion of the resistor 58. The resistor 58 is thus exposed to the environment surrounding the integrated circuit die 30. In one embodiment, the resistor 58 is formed from the fourth metal layer of the integrated circuit die 30. The resistor 58 is for example platinum or a platinum alloy. Contacts 72a and 72b electrically connect the resistor 58 to metal interconnections 46 of a third metal layer below the resistor 58. In operation, a current is passed through the resistor 58 through contacts 72a and 72b. Because the resistance of the resistor 58 varies with temperature, the magnitude of the current flowing in the resistor 58 is indicative of the temperature in the environment surrounding the integrated circuit die 30. Therefore the current flowing in the resistor 58 is an analog temperature signal.

Figure 12A:
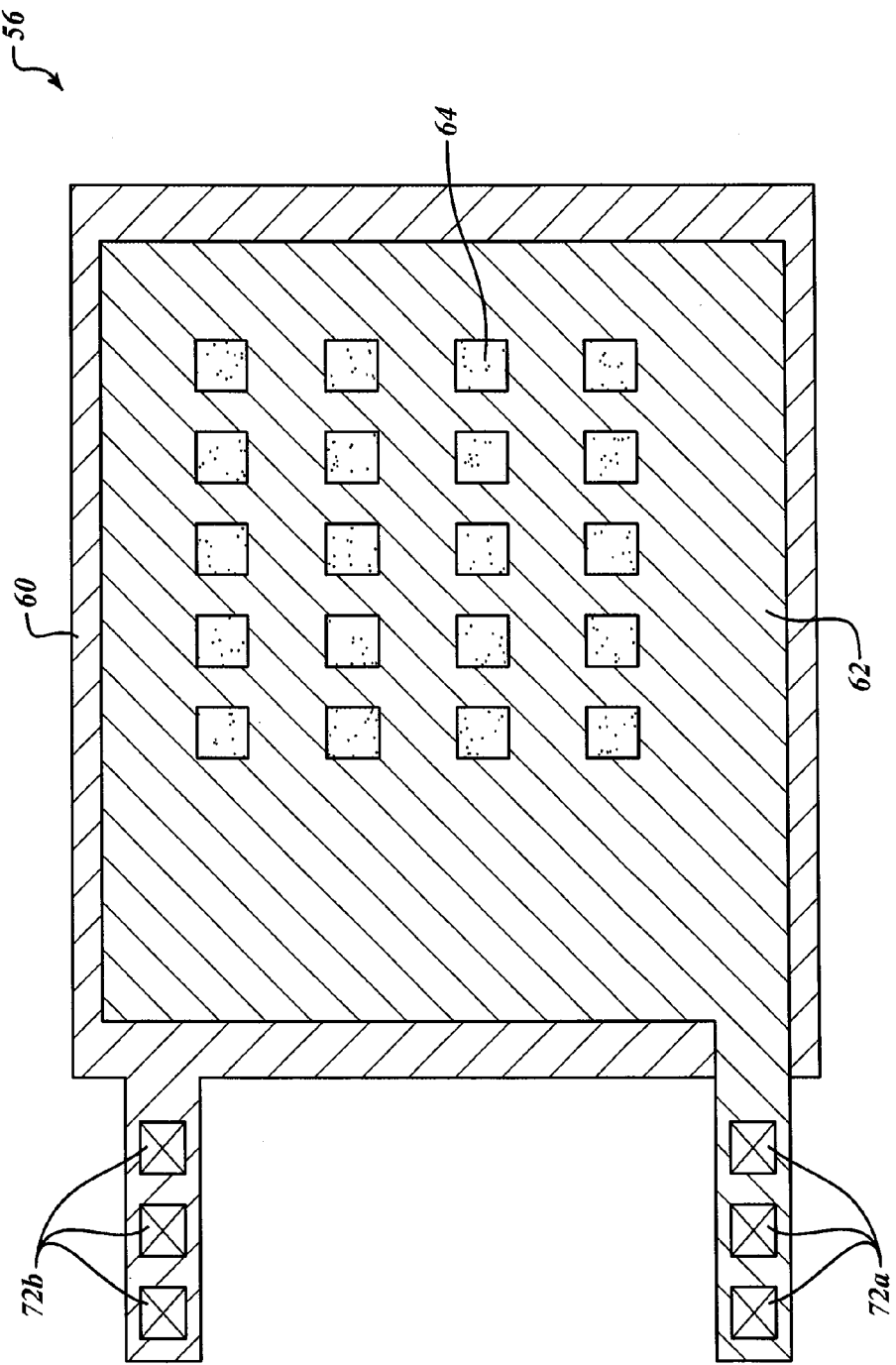
FIG. 12A is a top view of a humidity sensor according to one embodiment.

FIG. 12A is a top view of a humidity sensitive capacitor 56 according to one embodiment. As described previously, the humidity sensitive capacitor 56 includes a top plate 62 above a bottom plate 60. The top plate 62 is exposed to the environment surrounding the integrated circuit die 30 by removing a portion of the molding compound 52 over the top electrode 62. The molding compound 52 is not illustrated in FIG. 12A for clarity. A humidity sensitive layer 64 is between the bottom electrode 60 and the top electrode 62, as described previously. The humidity sensitive layer 64 is not illustrated in FIG. 12A except in openings etched in the top plate 62. The openings in the top plate 62 expose portions of the humidity sensitive layer 64 to the environment surrounding the integrated circuit die 30. Humidity in the air can thus enter into the humidity sensitive layer 64 causing a change in one or more characteristics of the humidity sensitive layer 64. In one embodiment the humidity sensitive layer 64 is a humidity sensitive dielectric layer whose dielectric constant varies with humidity. Thus a capacitance between the electrode 60 and the electrode 62 changes as the dielectric constant of the humidity sensitive dielectric layer 64 changes with the humidity. The capacitance between the top electrode 62 and the bottom electrode 60 is an analog humidity signal, as described previously. Contacts 72a electrically connect the top electrode 62 to electrical contacts 46 of the third metal layer. Contacts 72b electrically connect the bottom electrode 60 to the metal interconnections 46 of the third metal layer. The bottom electrode 60 is formed of the fourth metal layer, platinum. The top electrode 62 is formed of the fifth metal layer, gold. Many other shapes and configurations of the humidity sensitive capacitor 56 are possible and fall within the scope of the present disclosure.

Figure 12B:
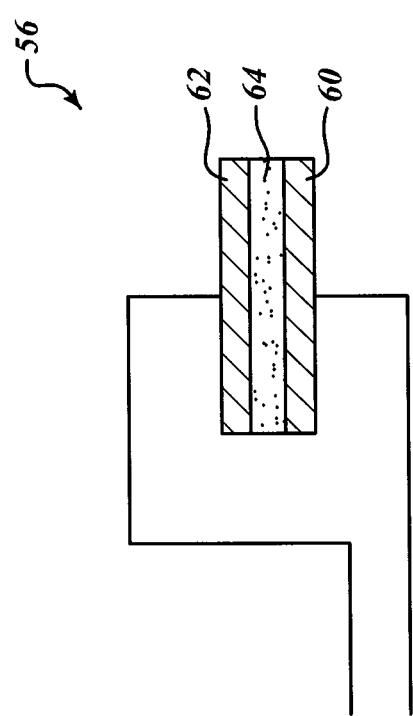
FIG. 12B is a schematic of a side view of the humidity sensor of FIG. 12A according to one embodiment.

FIG. 12B is a simplified schematic of the humidity sensitive capacitor 56 of FIG. 12A. The humidity sensitive layer 64 separates the bottom electrode 60 from the top electrode 62. Electrical connections connected to the bottom electrode 60 and the top electrode 62, respectively, can output an analog humidity signal from the capacitive humidity sensor 56.

Figure 13:
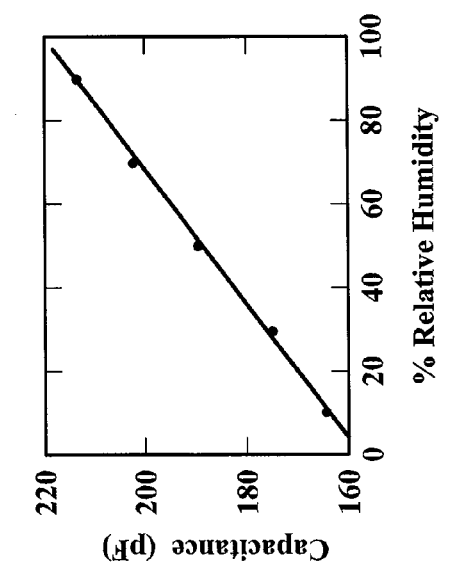
FIG. 13 is a graph of the capacitance of a humidity sensor as a function of relative humidity according to one embodiment.

FIG. 13 is a graph of the capacitance of the humidity sensitive capacitor 56 versus relative humidity of the environment surrounding the integrated circuit die 30 according to one embodiment. The capacitance of the humidity sensitive capacitor 56 varies between about 160 picofarads and 220 picofarads as the relative humidity varies between 0% and 100%. Thus, a capacitive signal output from the humidity sensitive capacitor 56 is indicative of the percentage of relative humidity in the environment surrounding the integrated circuit die 30. While the capacitance of the humidity sensitive capacitor 56 as shown in FIG. 13 varies linearly with temperature, in other embodiments, the capacitance of the humidity sensitive capacitor 56 may vary in a fashion other than linearly. For example, the capacitance of the humidity sensitive capacitor 56 may increase exponentially or logarithmically or may make sudden increases at certain temperatures depending on the materials and configuration of the capacitor 56.

Figure 14:
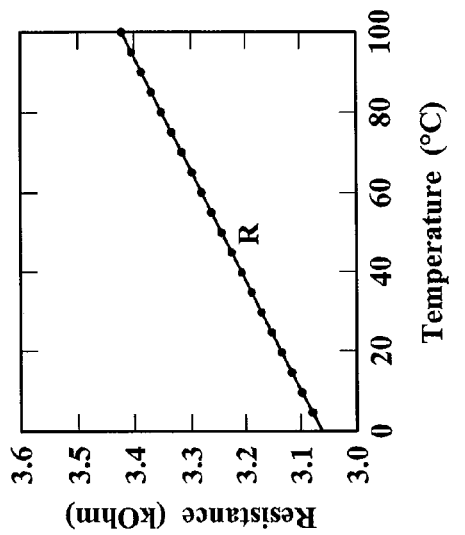
FIG. 14 is a graph of the resistance of a thermal sensor as a function of temperature according to one embodiment.

FIG. 14 is a graph of the resistance of a resistor 58 as described previously versus the temperature in degrees Celsius. As the temperature increases from about 0° C. to 100° C., the resistance of the resistor 58 also varies between about 3.1 kiloohms and 3.4 kiloohms. The resistance of the resistor 58 thus increases as the temperature increases. Thus an analog signal such as a voltage or a current signal from the resistor 58 is indicative of the temperature in the environment surrounding the integrated circuit die 30. While the resistance of the resistor 58 as shown in FIG. 14 varies linearly with temperature, in other embodiments, the resistance of the resistor 58 may vary in a fashion other than linearly. For example, the resistance of the resistor 58 may increase exponentially or logarithmically or may make sudden increases at certain temperatures. All such possibilities can be taken into account when calibrating the integrated circuit die 30 to detect a temperature.

Figure 15:
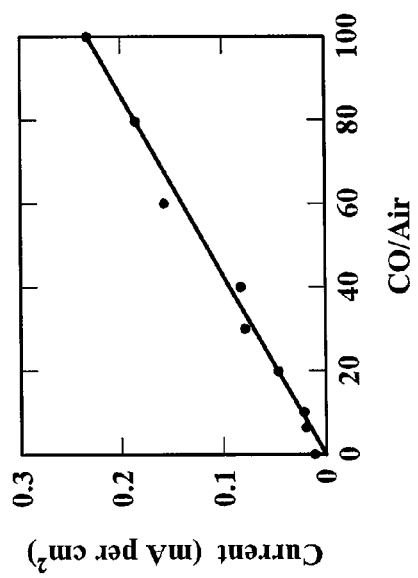
FIG. 15 is a graph of a current density of a chemical sensor as a function of CO concentration in air according to one embodiment.

FIG. 15 illustrates the current flowing between chemical sensor electrodes 32a and 32b versus the percentage of carbon monoxide in the air according to one embodiment. The current density flowing between the electrodes 32a and 32b varies between about 0 milliamps per centimeter squared to 0.2 milliamps per centimeter squared as the percentage of carbon monoxide in the air increases from 0% to 100%. Thus an analog current signal flowing in the chemical sensor electrodes 32a and 32b is indicative of the concentration of carbon monoxide in the environment surrounding the integrated circuit die 30. In other embodiments, the current density increases in a fashion other than linearly. For example, the current density can increase exponentially, logarithmically, or disjointedly based on the particular reactant 54 being used and the setup of the chemical sensing electrodes 32a, 32b.

Figure 16:
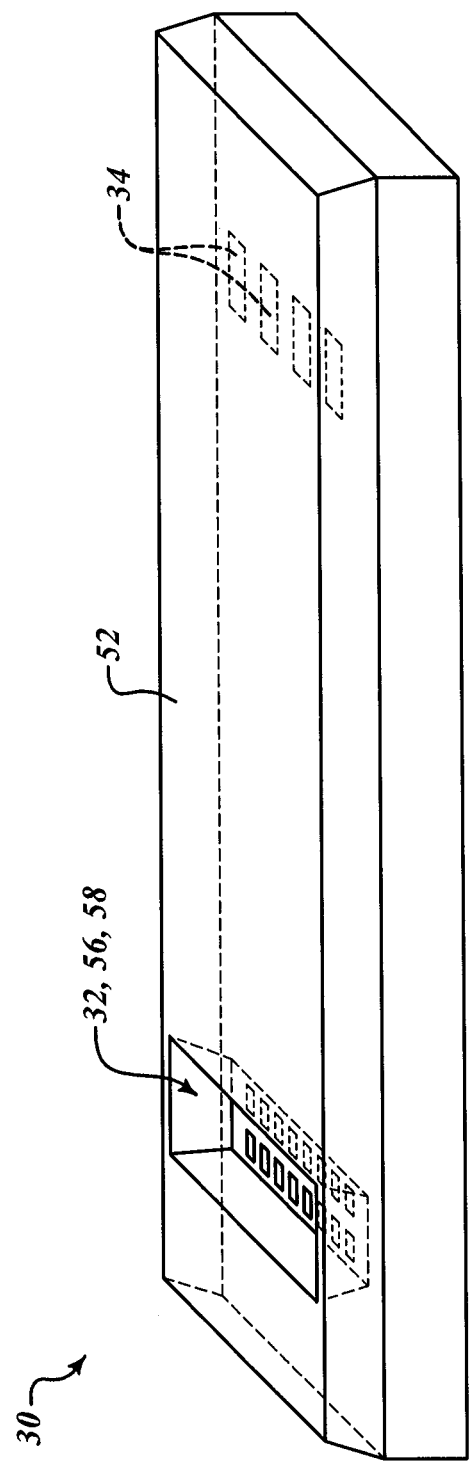
FIG. 16 is an elevated perspective view of an integrated circuit die according to one embodiment.

FIG. 16 illustrates an integrated circuit die 30 according to one embodiment. The integrated circuit die 30 is covered in a molding compound 52 as described previously. Chemical, thermal, and humidity sensors 32, 50, and 56 are formed in the integrated circuit die 30 as described previously. The molding compound 52 has been selectively removed to expose portions of electrodes 32, resistor 58, and humidity sensitive capacitor 56. Electrical contacts 34 are also formed in the integrated circuit die 30. The electrical contacts are covered by the molding compound 52 as shown in FIG. 16. In other embodiments, the electrical contacts 34 may be connected by wire bonding to leads of the integrated circuit package 30. The electrical contacts 34 may also be connected to ball grid arrays, pin grid arrays, embedded wafer level ball grid arrays, or other suitable connection schemes. The integrated circuit die of FIG. 16 can detect the presence or concentration of a selected chemical in the environment surrounding the integrated circuit die 30 as described previously. Analog to digital converter 33 and microcontroller 35 (not shown) are formed in the integrated circuit die 30 as described previously.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A integrated circuit die comprising:
   a semiconductor substrate;
   a plurality of transistors formed in the semiconductor substrate;
   a dielectric layer on the semiconductor substrate;
   metal interconnections in the dielectric layer;
   a first passivation layer on the dielectric layer;
   a first electrode on the first passivation layer;
   a second passivation layer over the first electrode and the first passivation layer;
   a first opening in the second passivation layer exposing a portion of the first electrode;
   a chemical reactant coating on the exposed portion of the first electrode, the reactant configured to react with a selected chemical in an environment surrounding the integrated circuit die, the reactant and the first electrode configured to generate an analog signal indicative of a concentration of the selected chemical in the environment surrounding the integrated circuit die; and
   a second electrode formed on the first passivation layer, a portion of the second electrode being coated in the chemical reactant and exposed to the surrounding environment by the first opening, wherein the analog signal is a current flowing between the first and the second electrode through the chemical reactant.

2. The integrated circuit die of claim 1 comprising a heat sensitive resistor on the first passivation layer, the heat sensitive resistor being configured to output a temperature signal indicative of a temperature of the environment surrounding the integrated circuit die.

3. The integrated circuit die of claim 2 including second opening in the second passivation layer exposing a portion of the heat sensitive resistor to the environment surrounding the integrated circuit die.

4. The integrated circuit die of claim 1 including a humidity sensor formed on the first passivation layer, the humidity sensor configured to output a humidity signal indicative of a humidity in the environment surrounding the integrated circuit die.

5. The integrated circuit die of claim 4 wherein the humidity sensor is a humidity sensitive capacitor comprising:
   a first capacitor plate formed on the first passivation layer;
   a humidity sensitive dielectric layer formed on the first capacitor plate; and
   a second capacitor plate formed on the humidity sensitive dielectric layer.

6. The integrated circuit die of claim 5 wherein a dielectric constant of the humidity sensitive dielectric layer depends on the humidity in the environment surrounding the integrated circuit die.

7. The integrated circuit die of claim 1 comprising a third electrode formed on the first passivation layer, a portion of the third electrode being coated in the reactant and exposed to the surrounding environment by the first opening.

8. The integrated circuit die of claim 1 comprising an analog to digital converter formed in the semiconductor substrate and being configured to receive the analog signal from the first electrode through the metal interconnections and to convert the analog signal to a digital signal.

9. The integrated circuit die of claim 8 including a microcontroller formed in the semiconductor substrate and being configured to receive the digital signal from the analog to digital converter and to estimate a value of the concentration of the selected chemical based in part on the digital signal.

10. A integrated circuit die comprising:
    a semiconductor substrate;
    a first passivation layer on the semiconductor substrate;
    a second passivation layer on the first passivation layer;
    a first opening in the second passivation layer; and
    a chemical sensor formed on the first passivation layer, the chemical sensor configured to sense a presence of a selected chemical and to output an analog signal indicative of a concentration of the selected chemical in an environment surrounding the integrated circuit diet, the chemical sensor including:
      a first electrode on the first passivation layer and exposed by the first opening;
      a second electrode formed on the first passivation layer and exposed by the first opening; and
      a chemical reactant coating positioned in the first opening in contact with the first electrode and second electrodes, the reactant configured to react with a selected chemical in an environment surrounding the integrated circuit die, wherein the analog signal is a current flowing between the first and the second electrode through the chemical reactant.

11. The integrated circuit die of claim 10 comprising:
a humidity sensor formed on the first passivation layer; and
a second opening in the second passivation layer exposing a portion the humidity sensor to the environment surrounding the integrated circuit die.

12. The integrated circuit die of claim 11 wherein the humidity sensor includes:
a first capacitor plate on the first passivation layer;
a humidity sensitive dielectric layer on the first capacitor plate; and
a second capacitor plate on the humidity sensitive dielectric layer.

13. The integrated circuit die of claim 10 comprising:
a temperature sensor on the first passivation layer; and
a second opening in the second passivation layer exposing a portion the temperature sensor to the environment surrounding the integrated circuit die.

14. The integrated circuit die of claim 10 comprising:
an analog to digital converter formed in the semiconductor substrate; and
metal interconnections coupling the analog to digital converter to the chemical sensor, the chemical sensor configured to output the analog signal to the analog to digital converter, the analog to digital converter configured to convert the analog signal to a digital signal.

15. The integrated circuit die of claim 14 comprising a microcontroller formed in the in the semiconductor substrate, the microcontroller being configured to receive the digital signal from the analog to digital converter and to compute a value of the concentration of the selected chemical.

16. The integrated circuit die of claim 15 wherein the microcontroller is configured to compute the concentration of the selected chemical based on the digital signal, a temperature signal, and a humidity signal.

17. A integrated circuit die comprising:
a semiconductor substrate;
a plurality of transistors formed in the semiconductor substrate;
a dielectric layer on the semiconductor substrate;
metal interconnections in the dielectric layer;
a first passivation layer on the dielectric layer;
a first electrode on the first passivation layer;
a second passivation layer over the first electrode and the first passivation layer;
a first opening in the second passivation layer exposing a portion of the first electrode;
a chemical reactant coating the exposed portion of the first electrode, the reactant configured to react with a selected chemical in an environment surrounding the integrated circuit die, the reactant and the first electrode configured to generate an analog signal indicative of a concentration of the selected chemical in the environment surrounding the integrated circuit die;
a heat sensitive resistor on the first passivation layer, the heat sensitive resistor being configured to output a temperature signal indicative of a temperature of the environment surrounding the integrated circuit die;
a second opening in the second passivation layer exposing a portion of the heat sensitive resistor to the environment surrounding the integrated circuit die; and
a capacitive humidity sensor configured to output a humidity signal indicative of a humidity in the environment surrounding the integrated circuit die, the capacitive humidity sensor including:
a first capacitor plate formed on the first passivation layer;
a humidity sensitive dielectric layer formed on the first capacitor plate; and
a second capacitor plate formed on the humidity sensitive dielectric layer.

18. The integrated circuit die of claim 17 wherein a dielectric constant of the humidity sensitive dielectric layer depends on the humidity in the environment surrounding the integrated circuit die.

19. The integrated circuit die of claim 17 comprising a second electrode formed on the first passivation layer, a portion of the second electrode being coated in the chemical reactant and exposed to the surrounding environment by the first opening.

20. The integrated circuit die of claim 19 wherein the analog signal is a current flowing between the first and the second electrode through the chemical reactant.

21. The integrated circuit die of claim 20 comprising a third electrode formed on the first passivation layer, a portion of the third electrode being coated in the reactant and exposed to the surrounding environment by the first opening.

22. The integrated circuit die of claim 17 comprising an analog to digital converter formed in the semiconductor substrate and being configured to receive the analog signal from the first electrode through the metal interconnections and to convert the analog signal to a digital signal.

* * * * *